(12) United States Patent
Kuang et al.

(10) Patent No.: US 9,351,978 B2
(45) Date of Patent: May 31, 2016

(54) NEUROGENESIS SCREENING METHOD AND USES THEREOF

(71) Applicant: Mead Johnson Nutrition Company, Glenview, IL (US)

(72) Inventors: Chenzhong Kuang, Newburgh, IN (US); Yan Xiao, Newburgh, IN (US); Dirk Hondmann, Winnetka, IL (US); Eduard Poels, Newburgh, IN (US); Zeina Jouni, Evansville, IN (US)

(73) Assignee: Mead Johnson Nutrition Company, Glenview, IL (US)

(*) Notice: Subject to any disclaimer, the term of this patent is extended or adjusted under 35 U.S.C. 154(b) by 0 days.

(21) Appl. No.: 14/044,916

(22) Filed: Oct. 3, 2013

(65) Prior Publication Data

US 2014/0179656 A1    Jun. 26, 2014

Related U.S. Application Data

(63) Continuation-in-part of application No. 13/408,485, filed on Feb. 29, 2012, and a continuation-in-part of application No. 13/408,490, filed on Feb. 29, 2012.

(51) Int. Cl.
*A61K 31/575* (2006.01)
*A23L 1/29* (2006.01)
*G01N 33/50* (2006.01)

(52) U.S. Cl.
CPC .............. *A61K 31/575* (2013.01); *A23L 1/296* (2013.01); *G01N 33/5058* (2013.01); *G01N 33/5073* (2013.01)

(58) Field of Classification Search
CPC .......... G01N 33/5058; G01N 33/5091; G01N 33/5073; A61K 31/575
USPC ............................................ 435/29; 514/182
See application file for complete search history.

(56) References Cited

U.S. PATENT DOCUMENTS

| | | | |
|---|---|---|---|
| 4,791,193 A | 12/1988 | Okonogi et al. | |
| 5,374,567 A | 12/1994 | Cartagena | |
| 5,397,591 A | 3/1995 | Kyle | |
| 5,550,156 A | 8/1996 | Kyle | |
| 5,849,885 A | 12/1998 | Nuyens | |
| 5,861,491 A | 1/1999 | Nuijens | |
| 5,919,913 A | 7/1999 | Nuyens | |
| 6,620,326 B1 | 9/2003 | Lihme et al. | |
| 6,977,046 B2 | 12/2005 | Hubbuch et al. | |
| 7,368,141 B2 | 5/2008 | Lihme | |
| 7,812,138 B2 | 10/2010 | Lihme et al. | |
| 7,867,541 B2 * | 1/2011 | McMahon et al. | 426/580 |
| 7,951,410 B2 | 5/2011 | McMahon et al. | |
| 2004/0265462 A1* | 12/2004 | Carlson | 426/580 |
| 2006/0210697 A1* | 9/2006 | Mower | 426/658 |
| 2012/0135103 A1 | 5/2012 | Walsh et al. | |
| 2012/0172288 A1* | 7/2012 | Wittke et al. | 514/2.5 |

FOREIGN PATENT DOCUMENTS

| | | |
|---|---|---|
| WO | 9200799 | 1/1992 |
| WO | 9717132 | 5/1997 |
| WO | 0218237 | 3/2002 |

OTHER PUBLICATIONS

Valenzuela et al. (2003). Cholesterol oxidatio: Health hazard and the role of antioxidants in prevention. Biol Res, v36, p. 291-302.*
Egg Nutrition facts: fatsecret.com, referencing USDA Nutritional Database SR18 (2010).*
Siega-Riz et al. (1998). Trends in breakfast consumption for children in the United States from 1965 to 1991. Am J Clin Nutr, v67(suppl), 748S-756S.*
Dewar (2008). Nutrients and calories in breast milk. From parentingscience.com.*
Lauber et al. (1979). Studies on the quality of breast milk during 23 months of lactation in a rural community of the Ivory Coast. Am J Clin Nutr, v32, p. 1159-1173.*
Hennart et al. (1991). Lysozyme, lactoferrin, and secretory immunoglobulin A content in breast milk: influence of duration of lactation, nutrition status, prolactin status, and parity of mother. Am J Clin Nutr, v53, p. 32-39.*
Johansson et al. (epub Feb. 2011). Low breast milk levels of long-chain n-3 fatty acids in allergic women, despite frequent fish intake. Clinical and Experimental Allergy, v41, p. 505-515 + 1 page for epub date.*
Scopesi et al. (2002). 7-Ketocholesterol in human and adapted milk formulas. Clinical Nutrition, v21(5), p. 379-384.*
Scopesi et al. 7-Ketocholesterol in human and adapted milk formulas. Clinical Nutrition (2002), v21(5), p. 379-384.*
Przygonski et al. Determination of cholesterol oxidation products in milk powder and infant formulas by gas chromatography and mass spectrometry. Nahrung (2000), v44 (2), p. 122-125.*
Orczewska-Dudek et al. Cholesterol and lipid peroxides in animal products and health implications—a review. Ann. Anim. Sci., vol. 12, No. 1 (2012) p. 25-52.*
Harris, J.J., et al., "The Energetics of CNS White Matter," J. Neurosci., Jan. 4, 2012; 32(1): 356-371.
Yadomae T., Structure and biological activities of fungal beta-1,3-glucans. Yakugaku Zasshi. 2000;120:413-431.

* cited by examiner

*Primary Examiner* — Scott Long
*Assistant Examiner* — Sean C Barron
(74) *Attorney, Agent, or Firm* — Patterson Intellectual Property Law, P.C; James R. Cartiglia; Bethany J. Whelan

(57) ABSTRACT

Provided herein are methods for detecting and/or confirming the neurogenesis effect of cholesterol and/or oxysterol utilizing adipose-derived stem cells (ADSCs). Further provided are methods of promoting neurogenesis in ADSCs. Also provided are methods for the use of cholesterol and/or oxysterol for the production of a neurologic component that may be incorporated into a nutritional composition for promoting neurogenesis in a pediatric subject.

13 Claims, 6 Drawing Sheets

NEUROGENESIS SCREENING METHOD AND USES THEREOF

TECHNICAL FIELD

The present disclosure relates to methods for detecting neurogenesis and/or methods for confirming the neurogenesis effect for cholesterol and/or oxysterol using adipose-derived stem cells (ADSCs), and more particularly, human adipose-derived stem cells (hADSCs). In some embodiments, the methods include detecting and/or confirming the neurogenesis effect for cholesterol or oxysterol using human neuronal stem cells.

Further, the present disclosure provides a method of use of cholesterol and/or oxysterol as a neurologic component for promoting neurogenesis in a pediatric subject by providing a nutritional composition including a neurologic component comprising cholesterol and/or oxysterol to a pediatric subject.

Additionally, the nutritional compositions disclosed herein may include docosahexaenoic acid ("DHA"), arachidonic acid ("ARA"), polydextrose ("PDX"), sialic acid, and mixtures thereof. Without being bound by any particular theory it is believed that when provided with the neurologic component described herein, these nutrients may provide synergistic neuronal health benefits.

BACKGROUND

The brain makes up only 2% of total body weight, yet it is a demanding organ that uses up to 30% of the day's calories and nutrients. (Harris, J. J. et al, *The Energetics of CNS White Matter*. Jour. of. Neuroscience, January 2012: 32(1): 356-371). The human brain and nervous system begin forming very early in prenatal life and both continue to develop until about the age of three. This early development can have lifelong effects on overall brain and nervous system health. Accordingly, brain nutrients can be important additives in the diets of infants, children and pregnant and lactating women because of their ability to promote early brain development and prevent and protect from brain and nervous system injury or illness. Additionally, brain nutrients are important for adults, as many nutrients promote nervous system repair and provide neuroprotective health benefits.

Brain nutrients have become increasingly important additives in the diets of infants, children and pregnant and lactating women because of their ability to promote early brain development. Additionally, compounds useful for treating neurodegenerative disease or brain injury are continuously being sought. Neuro-toxic compounds, such as environmental, industrial or dietary toxins, need to be identified in order to remove or reduce exposure to such compounds. Methods for discovering such nutrients and toxins are often extremely time consuming and inefficient. Accordingly, there is a need to provide a reliable, consistent, and fast method for identifying compounds having neurological development benefits. Additionally, there is need to identify compounds that are neurologically harmful.

It has been demonstrated that stem cells, such as adipose-derived stem cells (ADSCs), can be differentiated into multiple mature cell phenotypes, including neuronal cells, in a reproducible manner. In particular, this has been demonstrated in human adipose-derived stem cells (hADSCs). hADSCs are a particularly useful research tool because they are readily available from commercial resources or liposuction procedures, and they do not involve the same potential controversies that arise from the use of embryonic stem cells. Furthermore, hADSCs are easily obtained from an individual patient, thus providing an opportunity for personalized medicine.

Numerous nutrients are believed to be involved with supporting healthy brain development. Recently, however, it has been discovered that cholesterol and oxysterols promote neurogenesis and/or neuronal differentiation on human adipose-derived stem cells ("hADSCs") and human neuronal stem cells ("hNSCs").

BRIEF SUMMARY

One aspect of the present disclosure provides methods for detecting and/or confirming the neurogenesis effect of cholesterol using ADSCs. Another aspect of the present disclosure provides methods for detecting and/or confirming the neurogenesis effect of oxysterol using ADSCs. These methods are useful for confirming the neurological effect of cholesterol and oxysterol and, as such, may be used to supplement the diets of infants, children, and pregnant and lactating women.

Thus, in certain embodiments, the present disclosure provides a method for confirming the neurogenesis effect of cholesterol, comprising: culturing adipose-derived stem cells (ADSCs) in the presence of cholesterol; and determining the extent of neurogenesis in the ADSCs. The aforementioned method may further comprise culturing ADSCs in the absence of cholesterol, determining the extent of neurogenesis in the ADSCs cultured in the absence of cholesterol, and comparing the extent of neurogenesis in the ADSCs cultured in the presence of cholesterol to the extent of neurogenesis of the ADSCs cultured in the absence of cholesterol. In some embodiments, the adipose-derived stem cells are human adipose-derived stem cells (hADSCs).

In some embodiments, the present disclosure provides a method for confirming the neurogenesis effect of oxysterol, comprising: culturing adipose-derived stem cells (ADSCs) in the presence of oxysterol; and determining the extent of neurogenesis in the ADSCs. The aforementioned method may further comprise culturing ADSCs in the absence of oxysterol, determining the extent of neurogenesis in the ADSCs cultured in the absence of oxysterol, and comparing the extent of neurogenesis in the ADSCs cultured in the presence of oxysterol to the extent of neurogenesis of the ADSCs cultured in the absence of oxysterol.

In some embodiments, the disclosure is directed to the use of cholesterol, oxysterol, and combinations thereof, as a neurologic component for the promotion of neurogenesis in a subject, which can include providing a nutritional composition containing cholesterol and/or oxysterol and combinations thereof to a pediatric subject.

In some embodiments, the neurologic component comprising cholesterol, oxysterol or combinations thereof may be included in a nutritional composition and provided to the subject. The nutritional composition, in addition to the neurologic component, may further comprise a carbohydrate source, a fat source, and a protein source.

Without being bound by any particular theory, it is believed that an increase in the extent of neurogenesis in the ADSCs cultured in the presence of cholesterol and/or oxysterol compared to the extent of neurogenesis in the ADSCs cultured in the absence of cholesterol and/or oxysterol indicates that cholesterol and oxysterol are neurogenesis-promoting compounds.

In certain embodiments, the method further comprises culturing ADSCs in the presence of a known neurogenesis-promoting compound, such as docosahexaenoic acid (DHA), determining the extent of neurogenesis of the ADSCs cultured in the presence of DHA, and comparing the extent of neurogenesis in the ADSCs cultured in the presence of cholesterol and/or oxysterol to the extent of neurogenesis in the ADSCs cultured in the presence of DHA, wherein an increase in the extent of neurogenesis in the ADSCs cultured in the presence of cholesterol and/or oxysterol compared to the extent of neurogenesis in the ADSCs cultured in the presence of DHA indicates that cholesterol and/or oxysterol are superior neurogenesis-promoting compounds.

In certain embodiments, the extent of neurogenesis is determined by observing a change in cell morphology of the ADSCs. The change in cell morphology includes, without limitation, shrinkage of cell cytoplasm, formation of a neurite, formation a dendrite-like projection, formation of an axon, or any combination thereof. Changes in cell morphology can be determined by any method for cellular analysis or visualization. For example, the change in cell morphology can be observed by microscopy, such as phase contrast microscopy. In other embodiments, the extent of neurogenesis is determined by observing cellular biomarkers indicative of neurogenesis.

In any of the aforementioned methods, the ADSCs are cultured in the presence of cholesterol and/or oxysterol for a period of time sufficient for neurogenesis to occur, for example about 1 to about 5 days. Furthermore, the ADSCs may be cultured at an elevated temperature, such as from about 25° C. to about 45° C.

The cultureware used for culturing the ADSCs may comprise a coating that promotes or supports neurogenesis, such as a coating that mimics the environment of the central nervous. For example, the cultureware may comprise a coating comprising poly-L-ornithine and bovine fibronectin.

The medium used to culture the ADSCs, in some embodiments, promotes or supports neurogenesis. For example, the medium may comprise a neural basal medium, epidermal growth factor (EGF), basic fibroblast growth factor (b-FGF), N2 supplement, and L-glutamine.

In certain embodiments, the method comprises priming the ADSCs for about 1 to about 5 days in a priming medium prior to culturing the cells in the presence of the cholesterol or oxysterol. The priming medium may comprise a neural basal medium, EGF, b-FGF, and N2 supplement. After priming, the ADSCs may be cultured in a medium comprising MesenPRO complete and cholesterol or oxysterol for about 1 to about 5 days.

Another aspect of the present disclosure provides a method of promoting neurogenesis in ADSCs, comprising: culturing the ADSCs in the presence of cholesterol and/or oxysterol. In certain embodiments, the method further comprises determining the extent of neurogenesis in the ADSCs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
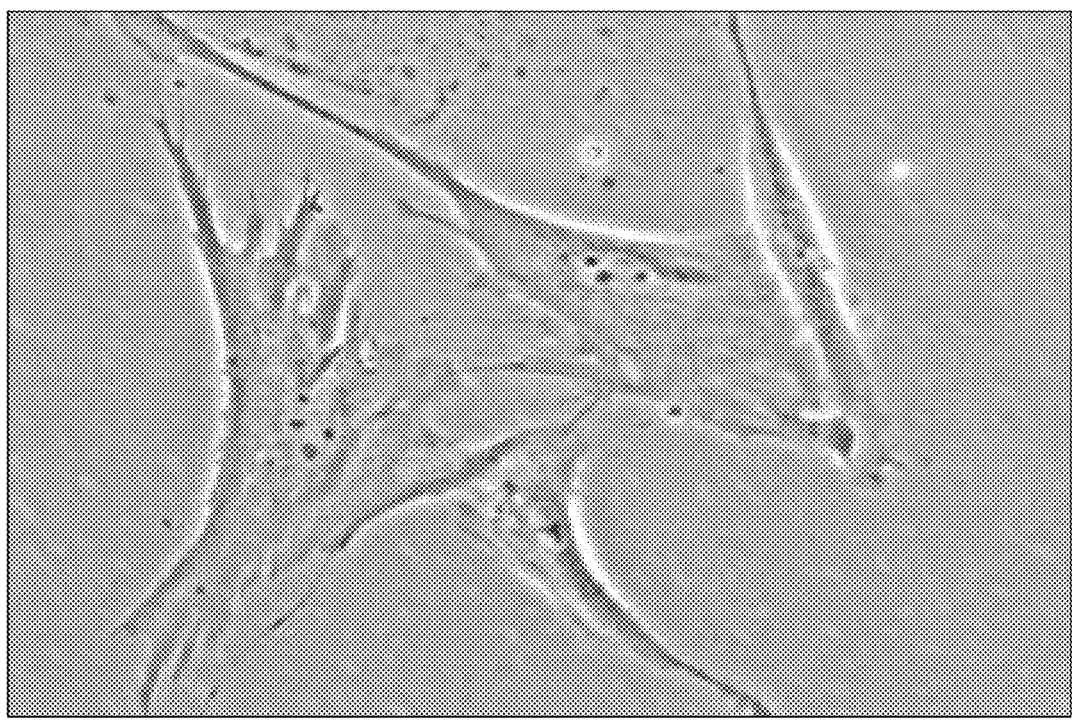
FIG. 1A is a phase contrast microscopy image of hADSCs under the neuronal differentiation condition without treatment. Morphology of hADSCs represents a condition of undifferentiation, with a large and flat morphology, as well as no obvious neurite outgrowth.

The present disclosure provides methods for detecting and/or confirming the neurogenesis effects of cholesterol comprising: culturing adipose-derived stem cells (ADSCs) in the presence of cholesterol, and determining the extent of neurogenesis in the ADSCs. Further, the present disclosure provides methods for detecting and/or confirming the neurogenesis effects of oxysterol comprising: culturing adipose-derived stem cells (ADSCs) in the presence of oxysterol, and determining the extent of neurogenesis in the ADSCs.

"Neurogenesis" refers to the differentiation, generation or proliferation of neural cells from stem or progenitor cells in vitro or in vivo. The extent of neurogenesis can be determined by a variety of techniques, such as by observing morphological changes in the cells. Any method for cellular analysis or visualization is suitable for use in the present methods. For example, morphological changes in the ADSCs may be observed using a microscopic technique, such as phase contrast microscopy. Morphological changes that indicate neurogenesis include, but are not limited to, shrinkage of cytoplasm and the presence of neurites, axons and dendrites. In other embodiments, the extent of neurogenesis is determined by observing cellular biomarkers indicative of neurogenesis, such as by using biomarker expression experiments. Examples of such biomarkers include, but are not limited to, proteins such as neurofilaments, myelin basic protein, microtubule associated protein 2 (MAP2), nestin, -III tubulin, glial fibrillar acidic protein (GFAP), S100 (a calcium binding protein), CNPase and GABA receptor.

A "neurogenesis-modulating compound" refers to a compound that affects neurogenesis, either by promoting or inhibiting neurogenesis. Thus, in some embodiments, neurogenesis-modulating compounds promote neurogenesis ("neurogenesis-promoting compounds"), while in other embodiments, the neurogenesis-modulating compounds inhibit or reduce neurogenesis ("neurogenesis-inhibiting compounds"). Compounds identified as promoting neurogenesis may advantageously be used as supplements in the diets of infants, children, and pregnant and lactating mothers in order to promote and support early brain development. These compounds also may be useful in treating neurodegenerative diseases or neurological injuries. Compounds identified as inhibiting neurogenesis may be potential toxins to be avoided or removed from the diets and environments of infants, children, and pregnant and lactating women. These compounds also may interfere with the treatment or healing of neurological diseases or injuries. Thus, neurogenesis-inhibiting compounds may also be avoided in the diets and environments of individuals suffering from neurological disease or injury.

"Nutritional composition" means a substance or formulation that satisfies at least a portion of a subject's nutrient requirements. The terms "nutritional(s)", "nutritional formula (s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults. The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

A "neurologic component" refers to a compound or compounds, or a composition, that affects neurogenesis, either by promoting or inhibiting neurogenesis. Thus, in some embodiments, a neurologic component promotes neurogenesis, while in other embodiments, a neurologic component inhibits or reduces neurogenesis, as compared to the degree of neurogenesis when the neurologic component is not provided.

"Pediatric subject" means a human less than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or fullterm) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, and preterm infants. "Preterm" means an infant born before the end of the 37$^{th}$ week of gestation. "Full term" means an infant born after the end of the 37$^{th}$ week of gestation.

"Child" means a subject ranging in age from 12 months to about 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

The term "degree of hydrolysis" refers to the extent to which peptide bonds are broken by a hydrolysis method. For example, the protein equivalent source of the present disclosure may, in some embodiments comprise hydrolyzed protein having a degree of hydrolysis of no greater than 40%. For this example, this means that at least 40% of the total peptide bonds have been cleaved by a hydrolysis method.

The term "partially hydrolyzed" means having a degree of hydrolysis which is greater than 0% but less than 50%.

The term "extensively hydrolyzed" means having a degree of hydrolysis which is greater than or equal to 50%.

"Probiotic" means a microorganism with low or no pathogenicity that exerts at least one beneficial effect on the health of the host.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

The term "inactivated probiotic" means a probiotic wherein the metabolic activity or reproductive ability of the referenced probiotic organism has been reduced or destroyed. The "inactivated probiotic" does, however, still retain, at the cellular level, at least a portion its biological glycol-protein and DNA/RNA structure. As used herein, the term "inactivated" is synonymous with "non-viable". More specifically, a non-limiting example of an inactivated probiotic is inactivated *Lactobacillus rhamnosus* GG ("LGG") or "inactivated LGG".

The term "cell equivalent" refers to the level of non-viable, non-replicating probiotics equivalent to an equal number of viable cells. The term "non-replicating" is to be understood as the amount of non-replicating microorganisms obtained from the same amount of replicating bacteria (cfu/g), including inactivated probiotics, fragments of DNA, cell wall or cytoplasmic compounds. In other words, the quantity of non-living, non-replicating organisms is expressed in terms of cfu as if all the microorganisms were alive, regardless whether they are dead, non-replicating, inactivated, fragmented etc.

"Prebiotic" means a non-digestible food ingredient that beneficially affects the host by selectively stimulating the growth and/or activity of one or a limited number of bacteria in the digestive tract that can improve the health of the host.

"β-glucan" means all β-glucan, including specific types of β-glucan, such as β-1,3-glucan or β-1,3;1,6-glucan. Moreover, β-1,3;1,6-glucan is a type of β-1,3-glucan. Therefore, the term "β-1,3-glucan" includes β-1,3;1,6-glucan.

As used herein, "non-human lactoferrin" means lactoferrin which is produced by or obtained from a source other than human breast milk. In some embodiments, non-human lactoferrin is lactoferrin that has an amino acid sequence that is different than the amino acid sequence of human lactoferrin. In other embodiments, non-human lactoferrin for use in the present disclosure includes human lactoferrin produced by a genetically modified organism. The term "organism", as used herein, refers to any contiguous living system, such as animal, plant, fungus or micro-organism.

"Inherent lutein" or "lutein from endogenous sources" refers to any lutein present in the formulas that is not added as such, but is present in other components or ingredients of the formulas; the lutein is naturally present in such other components.

All percentages, parts and ratios as used herein are by weight of the total formulation, unless otherwise specified.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

In certain embodiments, the method further comprises providing a negative control culture of ADSCs for comparison to cholesterol and/or oxysterol. Accordingly, the method further comprises culturing ADSCs in the absence of the cholesterol and/or oxysterol, determining the extent of neurogenesis in the ADSCs cultured in the absence of cholesterol and/or oxysterol, and comparing the extent of neurogenesis in the ADSCs cultured in the presence of cholesterol and/or oxysterol to the extent of neurogenesis of the ADSCs cultured in the absence of cholesterol and/or oxysterol. An increase in the extent of neurogenesis in the ADSCs cultured in the presence of cholesterol and/or oxysterol compared to the extent of neurogenesis in the ADSCs cultured in the absence of cholesterol and/or oxysterol indicates that cholesterol and/or oxysterol are neurogenesis-promoting compounds. The, the negative control culture provides additional information regarding the neurogenesis modulating properties of cholesterol and oxysterol.

In other embodiments, the method further comprises providing a positive control culture. Thus, the method further comprises culturing ADSCs in the presence a known neurogenesis-promoting compound, and determining the extent of neurogenesis in the ADSCs cultured in the presence of the neurogenesis-promoting compound. For example, DHA is known to promote early brain development and may be used as a positive control. Accordingly, the method may further comprise culturing ADSCs in the presence of DHA. An increase in the extent of neurogenesis in the ADSCs cultured in the presence of cholesterol or oxysterol compared to the extent of neurogenesis in the ADSCs cultured in the presence of DHA indicates that cholesterol and/or oxysterol are a superior neurogenesis-promoting compound than DHA.

During neurogenesis, the ADSCs may differentiate into neuronal cells, precursors to neuronal cells, and cells having neuronal properties. Accordingly, the extent of neurogenesis can be determined by observing morphological changes in the cells. Changes in cell morphology that are indicative of neurogenesis include, but are not limited to, shrinkage of cell cytoplasm, formation of a neurite, formation of a dendrite-like projection, formation of an axon, or a combination thereof. Other changes in cell morphology indicative of neurogenesis include development of a morphology that resembles bi-polar, tri-polar and multi-polar neuronal cells.

The aforementioned changes in cell morphology can be observed by a microscopic technique, such as by phase contrast microscopy. Phase contrast microscopy images of the ADSCs may be multiple times during the culturing of the ADSCs. For example, images may be taken prior to culturing with either cholesterol or oxysterol, and one or more times after addition of cholesterol and/or oxysterol, such as three hours after, and then once daily thereafter.

The extent of neurogenesis can further be determined by measuring the percentage of ADSCs exhibiting neuronal differentiation and the length of cytoplasmic projections in the cells, such as neurites, axons and dendrites. The percentage of ADSCs exhibiting neuronal differentiation and length of cytoplasmic projections can be measured using Image J open software with an appropriate plug-in.

Changes in cellular biomarkers occur during neurogenesis. Thus, in some embodiments, a cellular expression study for neuronal markers is used to determine the extent of neurogenesis. Examples of such biomarkers include, but are not limited to, proteins such as neurofilaments, myelin basic protein, nestin, III tubulin, glial fibrillar acidic protein (GFAP), S100 (a calcium binding protein), microtubule associated protein 2 (MAP2), CNPase and GABA receptor. Additional techniques for determining neuronal differentiation include immunohisotlogical staining for neuronal markers, neuronal excitability measurements and western blotting for the expression of neural proteins.

In some embodiments, the ADSCs are human adipose-derived stem cells (hADSCs). hADSCs can advantageously be maintained in culture and readily passaged to provide multiple sub-cultures. Furthermore, hADSCs are readily available because they can be isolated from human adipose tissue collected during routine liposuction procedures and cryopreserved. hADSCs have the additional advantage of being readily obtained from an individual patient. The hADSCs thus obtained can be used in the methods described herein to screen a candidate compound, such as cholesterol or oxysterol, for individualized use. Accordingly, personalized and optimized nutrition, drug treatment, or determination of sensitivity to neurotoxins can be achieved using the methods of the present disclosure.

The ADSCs may be cultured for a sufficient amount of time for neurogenesis to occur. Neurogenesis may be observed at varying times, depending on the brain nutrient tested. Thus, in some embodiments, neurogenesis may be observed after a few hours of culturing while in other embodiments, neurogenesis may be observed after several days of culturing. For example, the ADSCs may be cultured for about 1 hour to about 5 days, about 1 hour to about 3 days, about 3 hours to about 36 hours, about 12 hours to about 24 hours, or about 24 to about 36 hours. Furthermore, culturing of ADSC's may be continued for one, two, three or four weeks in order to achieve a more complete neuronal differentiation. The culturing of the ADSCs may further be performed at an elevated temperature, such as a temperature above room temperature. Such temperatures include about 25 to about 45° C., about 30 to about 40° C., or about 37° C.

In the aforementioned methods, the ADSCs may advantageously be cultured in a medium that supports or promotes neurogenesis, for example by guiding the ADSCs to differentiate into neuronal cells. In some embodiments, the medium comprises a neural basal medium, epidermal growth factor (EGF), basic fibroblast growth factor b-FGF, N2 supplement and L-glutamine. The ingredients for the culture medium are available from commercial sources. For example, the neural basal medium can be Neurobasal™ Medium, which is available from Invitrogen. Neural Basal Medium™ may include the ingredients listed in Table 1:

TABLE 1

| Neurobasal ™ Medium | | | |
|---|---|---|---|
| Components | Molecular Weight | Concentration (mg/L) | mM |
| Amino Acids | | | |
| Glycine | 75 | 30 | 0.4 |
| L-Alanine | 89 | 2 | 0.0225 |
| L-Arginine hydrochloride | 211 | 84 | 0.398 |
| L-Asparagine-H2O | 150 | 0.83 | 0.00553 |
| L-Cysteine | 121 | 31.5 | 0.26 |
| L-Histidine hydrochloride-H2O | 210 | 42 | 0.2 |
| L-Isoleucine | 131 | 105 | 0.802 |
| L-Leucine | 131 | 105 | 0.802 |

TABLE 1-continued

| Neurobasal ™ Medium | | | |
|---|---|---|---|
| Components | Molecular Weight | Concentration (mg/L) | mM |
| L-Lysine hydrochloride | 183 | 146 | 0.798 |
| L-Methionine | 149 | 30 | 0.201 |
| L-Phenylalanine | 165 | 66 | 0.4 |
| L-Proline | 115 | 7.76 | 0.0675 |
| L-Serine | 105 | 42 | 0.4 |
| L-Threonine | 119 | 95 | 0.798 |
| L-Tryptophan | 204 | 16 | 0.0784 |
| L-Tyrosine | 181 | 72 | 0.398 |
| L-Valine | 117 | 94 | 0.803 |
| Vitamins | | | |
| Choline chloride | 140 | 4 | 0.0286 |
| D-Calcium pantothenate | 477 | 4 | 0.00839 |
| Folic Acid | 441 | 4 | 0.00907 |
| Niacinamide | 122 | 4 | 0.0328 |
| Pyridoxine hydrochloride | 204 | 4 | 0.0196 |
| Riboflavin | 376 | 0.4 | 0.00106 |
| Thiamine hydrochloride | 337 | 4 | 0.0119 |
| Vitamin B12 | 1355 | 0.0068 | 0.000005 |
| i-Inositol | 180 | 7.2 | 0.04 |
| Inorganic Salts | | | |
| Calcium Chloride (CaCl2) (anhyd.) | 111 | 200 | 1.8 |
| Ferric Nitrate (Fe(NO3)3"9H2O) | 404 | 0.1 | 0.000248 |
| Magnesium Chloride (anhydrous) | 95 | 77.3 | 0.814 |
| Potassium Chloride (KCl) | 75 | 400 | 5.33 |
| Sodium Bicarbonate (NaHCO3) | 84 | 2200 | 26.19 |
| Sodium Chloride (NaCl) | 58 | 3000 | 51.72 |
| Sodium Phosphate monobasic (NaH2PO4—H2O) | 138 | 125 | 0.906 |
| Zinc sulfate (ZnSO4—7H2O) | 288 | 0.194 | 0.000674 |
| Other Components | | | |
| D-Glucose (Dextrose) | 180 | 4500 | 25 |
| HEPES | 238 | 2600 | 10.92 |
| Sodium Pyruvate | 110 | 25 | 0.227 |

N2 supplement may be purchased from Invitrogen. The Invitrogen N2 supplement may comprise the following ingredients:

TABLE 2

| N2 Supplement | | | |
|---|---|---|---|
| Components | Molecular Weight | Concentration (mg/L) | mM |
| Proteins | | | |
| Human transferrin (Holo) | 10000 | 10000 | 1 |
| Insulin recombinant full chain | 5807.7 | 500 | 0.0861 |
| Other components | | | |
| Progesterone | 314.47 | 0.63 | 0.002 |
| Putrescine | 161 | 1611 | 10.01 |
| selenite | 173 | 0.52 | 0.00301 |

For example, the medium may comprise about 1 to about 100, about 5 to about 50, about 10 to about 25 or about 20 ng/mL of EGF. The medium further comprises about 1 to about 100 ng/mL, about 5 to about 50, about 10 to about 25, or about 20 ng/mL of b-FGF. The N2 supplement may be present in the medium at a concentration of about 1×, and L-glutamine may be present in an amount of about 0.1 to about 10 mM, about 1 to about 5 mM, or about 1.3 to about 3 mM. The medium may further comprise a suitable amount of cholesterol and/or oxysterol, for example from about 0.1 nM to about 10 mM, or 1 nM to about 1 mM.

In certain embodiments, the culturing medium is substantially free of serum or, preferably, completely free of serum. A culture medium substantially free of serum refers to medium having less than about 10% serum, more particularly less than about 2% or 0.1% serum; in certain embodiments, substantially free of serum refers to less than about 0.5% serum. A culture medium completely free of serum has 0% serum. While not being bound by any particular theory, it is believed serum may contain inconsistent and undetermined amounts of growth factors, which has the potential to impact the extent of neurogenesis. Accordingly, serum-free media eliminate the effects of serum on the extent of neurogenesis. Neurogenesis observed in ADSCs cultured in serum-free media can thus be attributed to cholesterol or oxysterol rather than the presence of serum.

The aforementioned methods are useful in a rapid neuronal differentiation platform ("RNDP"). The RNDP may advantageously be used to quickly screen large numbers of potential neurogenesis modulating compounds. Compounds can be rapidly screened using multi-well plates and/or by testing several compounds at once or libraries of compounds for high through-put results. Compounds identified in the RNDP are further investigated using an extended platform, if desired.

An extended neuronal differentiation protocol ("ENDP") further comprises a priming step. The ENDP is useful to further investigate and confirm the results of an RNDP. While not being bound by any particular theory, it is believed that priming the ADSCs allows for improved neuronal morphology, thereby providing additional insight in the neurogenesis modulating potential of a given compound. Accordingly, in some embodiments, the ADSCs are primed prior to culturing in the presence of cholesterol and/or oxysterol. For example, the ADSCs can be primed for about 1 to about 5 days in a suitable priming medium prior to culturing with either cholesterol or oxysterol. In other embodiments, the ADSCs are primed for about 1 to about 3 days, or for about 3 days.

In some embodiments, the priming medium comprises a neural basal medium (such as Neurobasal Medium™ from Invitrogen), with suitable concentrations of EGF, b-FGF, and N2 supplement. Suitable concentrations of EGF include about 1 to about 100 ng/mL, about 5 to about 50, about 10 to about 25 or about 20 ng/mL. Suitable concentrations of b-FGF include about 1 to about 100, about 5 to about 50, about 10 to about 25, or about 20 ng/mL of b-FGF. The N2 supplement may be present in the medium at a concentration of about 1×. The priming medium may be substantially free of serum or, more preferably, completely free of serum. A priming medium substantially free of serum refers to medium having less than about 10% serum, for example less than about 2% or 0.1% serum, while a culture medium completely free of serum has 0% serum. Furthermore, the priming medium may be free of or substantially free of cholesterol and/or oxysterol.

In embodiments wherein the ADSCs are primed prior to being cultured in the presence of cholesterol and/or oxysterol, the ADSCs are subsequently cultured in a suitable culture medium for about 1 to about 5 days. In other embodiments, the ADSCs are cultured for about 1 to about 3 days, or for about 3 days. After priming, the priming medium is removed and a culturing medium is added to the ADSCs. The culture medium comprises, for example, MesenPRO complete, available from Invitrogen. The culture medium may further comprise a suitable amount of cholesterol or oxysterol, for example about 0.1 nM to about 10 mM, or 1 nM to about 1 mM of cholesterol or oxysterol. In a negative control experiment, the culture medium is free of or substantially free of cholesterol and/or oxysterol. In a positive control experiment, the culture medium comprises a known neurogenesis promoting compound, such as DHA.

In some embodiments, the cultureware used to culture the ADSCs is coated with a unique combination of matrix proteins designed to mimic the in vivo environment of the central nervous system, maximize cellular neuronal differentiation activity, and enhance cellular attachment. In one embodiment, the coating comprises poly-L-ornithine and bovine plasma fibronectin. The coated cultureware can be prepared by contacting the cultureware with a solution of poly-L-ornithine and a solution of bovine fibronectin. The contacting steps may be performed in any order, simultaneously, or substantially simultaneously. For example, the cultureware can be contacted with the poly-L-ornithine prior to the bovine fibronectin or after the fibronectin. Alternatively, the poly-L-ornithine and bovine fibronectin are contacted with the cultureware simultaneously or substantially simultaneously.

Another aspect of the disclosure relates to an in vitro method of promoting neurogenesis in ADSCs comprising: culturing the ADSCs in the presence of a neurogenesis-promoting compound. Neuronal cells and neuron-like cells generated by the aforementioned methods may be maintained in culture, passaged, or cryopreserved. The method thus can provide human neuronal cells and neuron-like cells for use in the laboratory, such as for drug screening. In some embodiments, the method further comprises determining the extent of neurogenesis in the ADSCs, as described in the aforementioned screening methods.

Another aspect of the disclosure relates to a system for identifying a neurogenesis-modulating compound, comprising: ADSCs; cultureware comprising coating that mimics the central nervous system; and a culture medium. In some embodiments, the coating comprises bovine fibronectin and poly-L-ornithine. In systems useful in the RNDP, the culture medium the culture medium comprises a neural basal medium, EGF, b-FGF, N2 supplement, and L-glutamine. Systems useful in the ENDP, further comprise a priming medium, such as a medium comprising a neural basal medium, EGF, b-FGF, N2 supplement, and culture medium comprising MesenPRO Complete.

In some embodiments, the disclosure is directed to a method of use of cholesterol or oxysterols and combinations thereof as a neurologic component for promoting neurogenesis in a pediatric subject. In some embodiments, the neurologic component is incorporated into a nutritional composition and provided to a pediatric subject.

As noted above, the neurologic component may be selected from the group consisting of cholesterol, at least one oxysterol, and mixtures thereof. Cholesterol may be present in nutritional composition, in some embodiments in an amount from about 1 mg/100 kcal to about 100 mg/100 kcal. In other embodiments, cholesterol is present in the nutritional composition from about 5 mg/100 kcal to about 25 mg/100 kcal. In other embodiments cholesterol is present from about 15 mg/100 kcal to about 40 mg/100 kcal. In still other embodiments, cholesterol is present in the nutritional composition from about 50 mg/100 kcal to about 75 mg/100 kcal.

In some embodiments, at least one oxysterol may comprise the neurologic component. In some embodiments, where at least one oxysterol is the neurologic component, the at least one oxysterol may be present in the nutritional composition in an amount of from about 1 mg/100 kcal to about 100 mg/100 kcal. In other embodiments, the at least one oxysterol is present in the nutritional composition from about 5 mg/100 kcal to about 25 mg/100 kcal. In other embodiments the at least one oxysterol is present from about 15 mg/100 kcal to about 40 mg/100 kcal. In still other embodiments, the at least one oxysterol is present in the nutritional composition from about 50 mg/100 kcal to about 75 mg/100 kcal.

In still other embodiments, the nutritional composition may comprise a neurologic component that includes both cholesterol and at least one oxysterol. In some embodiments, the combination of cholesterol and at least one oxysterol may be present in the nutritional composition in an amount of from about 1 mg/100 kcal to about 200 mg/100 kcal. In other embodiments, cholesterol and at least one oxysterol are present in the nutritional composition from about 5 mg/100 kcal to about 150 mg/100 kcal. In other embodiments cholesterol and oxysterol are present from about 15 mg/100 kcal to about 100 mg/100 kcal. In still other embodiments, cholesterol and oxysterol are present in the nutritional composition from about 50 mg/100 kcal to about 75 mg/100 kcal.

Additionally, the nutritional composition may comprise a neurologic component comprising both cholesterol and at least on oxysterol in a combined amount of from about 1 mg/100 kcal to about 100 mg/100 kcal. In other embodiments, cholesterol and at least one oxysterol are present in the nutritional composition from about 5 mg/100 kcal to about 25 mg/100 kcal. In other embodiments cholesterol and at least one oxysterol are present from about 15 mg/100 kcal to about 40 mg/100 kcal. In still other embodiments, cholesterol and at least one oxysterol are present in the nutritional composition from about 50 mg/100 kcal to about 75 mg/100 kcal.

In embodiments where the neurologic component comprises both cholesterol and at least one oxysterol, cholesterol may comprise 1 wt. % to about 99 wt. % of the neurologic component and the at least one oxysterol may comprise 1 wt. % to about 99 wt. % of the neurologic component. In still other embodiments, the neurologic component may comprise from about 10 wt. % to about 90 wt. % cholesterol and 10 wt. % to about 90 wt. % of at least one oxysterol. In some embodiments, the neurologic component may comprise from about 20 wt. % to about 80 wt. % cholesterol and 20 wt. % to about 80 wt. % of at least one oxysterol. In some embodiments, the neurologic component may comprise from about 30 wt. % to about 70 wt. % cholesterol and 30 wt. % to about 70 wt. % of at least one oxysterol. In still other embodiments, the neurologic component may comprise from about 40 wt. % to about 60 wt. % cholesterol and 40 wt. % to about 60 wt. % of at least one oxysterol. In still other embodiments, the neurologic component may comprise from about 50 wt. % cholesterol and 50 wt. % of at least one oxysterol In one embodiment, cholesterol sources for the present disclosure include, but are not limited to, milk, other dairy products, eggs, meat, beef tallow, poultry, fish, shellfish and any other resources, fortified or not, from which cholesterol could be obtained and used in a nutritional composition. Sources of cholesterol also include precursors such as squalene, lanosterol, dimethylsterol, methosterol, lathosterol, and desmosterol. The cholesterol could be part of a complex mixture obtained by separation technology known in the art aimed at enrichment of the cholesterol and the derivatives or precursors of cholesterol in such mixtures.

Examples of oxysterols suitable for inclusion in the neurologic component of the nutritional composition include, but are not limited to 6β-epoxycholesterol, Cholestan-3β,5α,6β-triol, 4β-hydroxycholesterol, 7α-hydroxycholesterol, 7β-hydroxycholesterol, 7-ketocholesterol, 25-hydroxycholesterol Cholest-5-en-3β,25-diol, 27-hydroxycholesterol, 22(R)-hydroxycholesterol, 20 β-hydroxycholesterol, 24(S)-hydroxycholesterol, 24(S),25-epoxycholesterol, and 7α,25-hydroxycholesterol.

In some embodiments, the nutritional composition may comprise cholesterol and/or at least one oxysterol and further include at least one of the following: DHA, ARA, PDA, sialic acid, and mixtures thereof. It is believed that the combination of cholesterol and/or at least one oxysterol with at least one of these nutrients may synergistically promote neurogenesis. As used herein, when two or more compounds act "synergistic" or "synergistically", this means enhanced neurogenesis in the presence of the combination of compounds as compared to the neurogenesis observed by use of each compound individually.

The nutrients included in the neurologic component of the nutritional composition may be formulated with other ingredients in the nutritional composition to provide appropriate nutrient levels for the target subject. In some embodiments, the nutritional composition comprising a neurologic component is a nutritionally complete formula that is suitable to support normal growth and also benefit brain development. In certain other embodiments, the composition and concentration of the nutrients in the neurologic component are designed to mimic levels that are healthy for early human development.

The nutrients of the neurological component included in the nutritional composition may include functional equivalents, sources, metabolites and/or prerequisites. Such nutrients of the neurological component may be naturally-occurring, synthetic, or developed through the genetic manipulation of organisms and/or plants, whether such source is now known or developed later.

The source for the nutrients of the neurologic component described herein may be milk, other dairy products, soybean, including soybean oil, meats, eggs, cod, cod liver, herring, mackerel, salmon, menhaden, sardine, seaweed, wheat germ, including wheat germ oil, sugarcane extract, tomatoes, broccoli, brewer's yeast, organ meats, safflower oil, grapeseed oil, poppyseed oil, sunflower oil, hemp oil, corn oil, cottonseed oil, walnut oil, sesame oil, rice bran oil, pistachio oil, canola oil, linseed oil, lard, olive oil, palm oil, cocoa butter, macadamia oil, butter, coconut oil, other plants and any other resources, fortified or not, from which the nutrients of the neurologic component could be obtained and used in a nutritional composition. Preferably, the source for the nutrients of the neurologic component should be food grade having been food derived or microorganism produced. Additionally, the source of the nutrients of the neurologic component could be part of a complex mixture obtained by separation and purification technology known in the art aimed at enrichment of the derivatives or precursors of the neurologic component nutrient of such mixtures.

Further, some amounts of the nutrients in the neurologic component may be inherently present in known ingredients, such as natural oils, carbohydrate sources or proteins sources that are commonly used to make nutritional compositions. In some embodiments, the concentrations and ratios as described herein of the neurologic component are calculated based upon both added and inherent sources of the neurological component.

Additionally, the neurologic component may be added or incorporated into the nutritional composition by any method well known in the art. In some embodiments, the neurological component may be added to a nutritional composition to supplement the nutritional composition. For example, in one embodiment, the neurological component may be added to a commercially available infant formula. For example, Enfalac, Enfamil®, Enfamil® Premature Formula, Enfamil® with Iron, Enfamil® LIPIL®, Lactofree®, Nutramigen®, Pregestimil®, and ProSobee® (available from Mead Johnson Nutrition Company, Glenview, Ill., U.S.A.) may be supplemented with suitable levels of the neurologic component, and used in practice of the present disclosure.

In other embodiments, the neurologic component may be substituted for another nutrient source that does not contain the nutrients of the neurologic component. For example, a certain amount of a fat source that does not contain the neurological component may be substituted with another fat source that contains the nutrients of the neurological component. In still other embodiments, the source of an ingredient typically added to a nutritional composition may be altered, such that the source chosen provides both the ingredient that is commonly added to the nutritional composition and a nutrient of the neurological composition.

In some embodiments, the neurologic component may be included in prenatal dietary supplements. The neurologic component may be incorporated into prenatal dietary supplements by any method known in the art. The prenatal administration of the neurologic component may directly impact the development of the fetus and embryo. Since brain development begins early in prenatal life, the inclusion of the neurologic component in a prenatal dietary supplement may promote brain development and neurogenesis in pediatric subjects while still in utero.

Conveniently, commercially available prenatal dietary supplements and/or prenatal nutritional products may be used. For example, Expecta® Supplement (available from Mead Johnson Nutrition Company, Glenview, Ill., U.S.A.) may be supplemented with suitable levels of the neurologic component and used in practice of the present disclosure.

The prenatal dietary supplement may be administered in one or more doses daily. In some embodiments, the prenatal dietary supplement is administered in two doses daily. In a separate embodiment, the prenatal dietary supplement is administered in three daily doses. The prenatal dietary supplement may be administered to either pregnant women or women who are breastfeeding.

Any orally acceptable dosage form is contemplated by the present disclosure. Examples of such dosage forms include, but are not limited to pills, tablets, capsules, soft-gels, liquids, liquid concentrates, powders, elixirs, solutions, suspensions, emulsions, lozenges, beads, cachets, and combinations thereof. Alternatively, the prenatal dietary supplement of the invention may be added to a more complete nutritional product. In this embodiment, the nutritional product may contain protein, fat, and carbohydrate components and may be used to supplement the diet or may be used as the sole source of nutrition.

In some embodiments, the nutritional composition comprises at least one carbohydrate source. The carbohydrate source can be any used in the art, e.g., lactose, glucose, fructose, corn syrup solids, maltodextrins, sucrose, starch, rice syrup solids, and the like. The amount of the carbohydrate component in the nutritional composition typically can vary from between about 5 g/100 kcal and about 25 g/100 kcal. In some embodiments, the amount of carbohydrate is between about 6 g/100 kcal and about 22 g/100 kcal. In other embodiments, the amount of carbohydrate is between about 12 g/100 kcal and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

Moreover, the nutritional composition(s) of the disclosure may comprise at least one protein source. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate), soy bean proteins, and any combinations thereof.

In a particular embodiment of the nutritional composition, the whey:casein ratio of the protein source is similar to that found in human breast milk. In an embodiment, the protein source comprises from about 40% to about 85% whey protein and from about 15% to about 60% casein.

In some embodiments, the nutritional composition comprises between about 1 g and about 7 g of a protein source per 100 kcal. In other embodiments, the nutritional composition comprises between about 3.5 g and about 4.5 g of protein per 100 kcal.

In some embodiments, the proteins of the nutritional composition are provided as intact proteins. In other embodiments, the proteins are provided as a combination of both intact proteins and hydrolyzed proteins, with a degree of hydrolysis of between about 4% and 10%. In certain other embodiments, the proteins are more hydrolyzed. In still other embodiments, the protein source comprises amino acids. In yet another embodiment, the protein source may be supplemented with glutamine-containing peptides. In another embodiment, the protein component comprises extensively hydrolyzed protein. In still another embodiment, the protein component of the nutritional composition consists essentially of extensively hydrolyzed protein in order to minimize the occurrence of food allergy.

In some embodiments, the protein component of the nutritional composition comprises either partially or extensively hydrolyzed protein, such as protein from cow's milk. The proteins may be treated with enzymes to break down some or most of the proteins that cause adverse symptoms with the goal of reducing allergic reactions, intolerance, and sensitization. Moreover, the proteins may be hydrolyzed by any method known in the art.

In some embodiments, the nutritional composition of the present disclosure is substantially free of intact proteins. In this context, the term "substantially free" means that the preferred embodiments herein comprise sufficiently low concentrations of intact protein to thus render the formula hypoallergenic. The extent to which a nutritional composition in accordance with the disclosure is substantially free of intact proteins, and therefore hypoallergenic, is determined by the August 2000 Policy Statement of the American Academy of Pediatrics in which a hypoallergenic formula is defined as one which in appropriate clinical studies demonstrates that it does not provoke reactions in 90% of infants or children with confirmed cow's milk allergy with 95% confidence when given in prospective randomized, double-blind, placebo-controlled trials.

The nutritional composition may be protein-free in some embodiments and comprise free amino acids as a protein equivalent source. In some embodiments, the term "protein equivalent source" as used herein includes functional equivalents of protein(s), which exert beneficial health effects on a target subject without containing any intact protein. For example, "protein equivalent source" may include certain peptides and/or peptide fractions, amino acids, and combinations thereof. In certain embodiments, the protein source or sources incorporated into the nutritional composition may include both an intact protein source and protein equivalent source.

If included, in some embodiments, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In certain other embodiments, small amino acid peptides may be included as the protein component of the nutritional composition. Such small amino acid peptides may be naturally occurring or synthesized. The amount of free amino acids in the nutritional composition may vary from about 1 g/100 kcal to about 5 g/100 kcal.

The nutritional composition may also comprise a fat source. Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

The nutritional composition of the present disclosure may also contain a source of long chain polyunsaturated fatty acids ("LCPUFAs"). Suitable LCPUFAs include, but are not limited to DHA, ARA, linoleic (18:2 n-6), γ-linolenic (18:3 n-6), dihomo-γ-linolenic (20:3 n-6) acids in the n-6 pathway, α-linolenic (18:3 n-3), stearidonic (18:4 n-3), eicosatetraenoic (20:4 n-3), eicosapentaenoic ("EPA") (20:5 n-3), and docosapentaenoic (22:6 n-3).

The total amount of LCPUFA, including DHA and ARA, in the nutritional composition may be from about 5 mg/100 kcal to about 100 mg/100 kcal. In some embodiments the amount of LCPUFAs in the nutritional composition are from about 10 mg/100 kcal to about 50 mg/100 kcal.

Sources of LCPUFAs include dairy products like eggs and butterfat; marine oils, such as cod, menhaden, sardine, tuna and many other fish; certain animal fats, lard, tallow and microbial oils such as fungal and algal oils, or from any other resource fortified or not, form which LCPUFAs could be obtained and used in a nutritional composition. The LCPUFA could be part of a complex mixture obtained by separation technology known in the art aimed at enrichment of LCPUFAs and the derivatives or precursors of LCPUFAs in such mixtures.

The LCPUFAs may be provided in the nutritional composition in the form of esters of free fatty acids; mono-, di- and tri-glycerides; phosphoglyerides, including lecithins; and/or mixtures thereof. Additionally, LCPUFA may be provided in the nutritional composition in the form of phospholipids, especially phosphatidylcholine.

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the weight ratio of ARA:DHA is from about 1:2 to about 4:1.

Specifically, DHA may be present in the nutritional composition, in some embodiments, from about 5 mg/100 kcal to about 75 mg/100 kcal. In some embodiments, DHA is present in an amount from about 10 mg/100 kcal to about 50 mg/100 kcal. In still other embodiments, DHA may be present in an amount from about 15 mg/100 kcal to about 30 mg/100 kcal.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

Furthermore, some embodiments of the nutritional composition may mimic certain characteristics of human breast milk. However, to fulfill the specific nutrient requirements of some subjects, the nutritional composition may comprise a higher amount of some nutritional components than does human milk. For example, the nutritional composition may comprise a greater amount of DHA than does human breast milk. The enhanced level of DHA of the nutritional composition may compensate for an existing nutritional DHA deficit.

The nutritional composition may also contain one or more prebiotics (also referred to as a prebiotic source) in certain embodiments. Prebiotics can stimulate the growth and/or activity of ingested probiotic microorganisms, selectively reduce pathogens found in the gut, and favorably influence the short chain fatty acid profile of the gut. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides. In some embodiments, the total amount of prebiotics present in the nutritional composition may be from about 0.1 g/100 kcal to about 1 g/100 kcal. In certain embodiments, the total amount of prebiotics present in the nutritional composition may be from about 0.3 g/100 kcal to about 0.7 g/100 kcal. Moreover, the nutritional composition may comprise a prebiotic component comprising PDX and/or galacto-oligosaccharide ("GOS"). In some embodiments, the prebiotic component comprises at least 20% GOS, PDX or a mixture thereof.

If PDX is used in the prebiotic composition, the amount of PDX in the nutritional composition may, in an embodiment, be within the range of from about 0.1 g/100 kcal to about 1 g/100 kcal. In another embodiment, the amount of polydextrose is within the range of from about 0.2 g/100 kcal to about 0.6 g/100 kcal. And in still other embodiments, the amount of PDX in the nutritional composition may be from about 0.1 mg/100 kcal to about 0.5 mg/100 kcal or about 0.3 mg/100 kcal.

If GOS is used in the prebiotic composition, the amount of GOS in the nutritional composition may, in an embodiment, be from about 0.1 g/100 kcal to about 1 g/100 kcal. In another embodiment, the amount of GOS in the nutritional composition may be from about 0.2 g/100 kcal to about 0.5 g/100 kcal. In other embodiments, the amount of GOS in the nutritional composition may be from about 0.1 mg/100 kcal to about 1.0 mg/100 kcal or from about 0.1 mg/100 kcal to about 0.5 mg/100 kcal.

In a particular embodiment of the nutritional composition, PDX is administered in combination with GOS. In this embodiment, PDX and GOS can be administered in a ratio of PDX:GOS of between about 9:1 and 1:9. In another embodiment, the ratio of PDX:GOS can be between about 5:1 and 1:5. In yet another embodiment, the ratio of PDX:GOS can be between about 1:3 and 3:1. In a particular embodiment, the ratio of PDX to GOS can be about 5:5. In another particular embodiment, the ratio of PDX to GOS can be about 8:2.

In a particular embodiment, GOS and PDX are supplemented into the nutritional composition in a total amount of at least about 0.2 mg/100 kcal or about 0.2 mg/100 kcal to about 1.5 mg/100 kcal. In some embodiments, the nutritional composition may comprise GOS and PDX in a total amount of from about 0.6 to about 0.8 mg/100 kcal.

In some embodiments the nutritional composition comprises sialic acid. Sialic acids are a family of over 50 members of 9-carbon sugars, all of which are derivatives of neuoaminic acid. Sialic acids are found in milk, such as bovine and caprine. In mammals, neuronal cell membranes have the highest concentration of sialic acid compared to other body cell membranes.

The most common member of the sialic acid family is N-acetyl-neuraminic acid or 2-keto-acetamindo-3,5-dideoxy-D-glycero-D-galctononulopyranos-1-onic acid, often abbreviated Neu5Ac, NeuAc, or NANA. A second member of the family is N-glycolyl-neuraminic acid, abbreviated Neu5Ge or NeuGe, in which the N-acetyl group of NeuAc is hydroxylated. A third sialic acid family member is 2-keto-3-deoxy-nonulosonic acid, ("KDN"). Also included are O-substituted sialic acids such as 9-O—C1C6 acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac.

Non-limiting suitable sources for the sialic acids of the present disclosure include free sialic acid, such as NANA, as well as sialic acid complexed to oligosaccharides, glyocoproteins, and gangliosides. Since oligosaccharides are polymers of varying numbers of residues, linkages, and subunits; the number of different possible stereoisomeric oligosaccharide chains is enormous. Therefore, if sialic acid is in complex with an oligosaccharide, the nutritional compositions of the present disclosure may utilize sialic with any form of sugar moiety, either naturally found or artificially formulated from simple to complex.

Sialic acid residues are also known to be components of gangliosides. Gangliosides are a class of glycolipids, which generally consist of three elements. These elements include one or more sialic acid residues that are attached to an oligosaccharide or carbohydrate core moiety, which is attached to a hydrophobic lipid structure, such as a ceramide, which generally is embedded in the cell membrane. The ceramide portion includes a long chain base portion and a fatty acids portion.

Additionally, U.S. patent application Ser. No. 10/964,290, now U.S. Pat. No. 7,951,410 discloses a caseinoglycomacropeptide ("cGMP") having an enhanced concentration of sialic acid and a cGMP having an enhanced concentration of sialic acid and a reduced level of threonine. The disclosure of U.S. Pat. No. 7,951,410 is incorporated in its entirety herein. Accordingly, in some embodiments, the nutritional compositions of the present disclosure may include cGMP having an enhanced concentration of sialic acid.

If included in the nutritional composition, sialic acid may be present in an amount from about 0.5 mg/100 kcals to about 45 mg/100 kcal. In some embodiments sialic acid may be present in an amount from about 5 mg/100 kcals to about 30 mg/100 kcals. In still other embodiments, sialic acid may be present in an amount from about 10 mg/100 kcals to about 25 mg/100 kcals.

Without being bound by any particular theory, it is believed that DHA, ARA, PDX and/or sialic acid in combination with the neurologic component may have additive and/or synergistic brain and nervous system health benefits. In certain embodiments, the nutritional composition comprising DHA, ARA, PDX, and/or sialic acid and mixtures thereof can act synergistically with cholesterol and/or at least one oxysterol in the neurologic component to promote neurogenesis in nervous cell tissues.

The nutritional composition(s) of the present disclosure may optionally include N-ocatnoyl-D-threo-sphingosine. If included in the nutritional composition, N-octanoyl-D-threo-sphingosine, may be present in an amount from about 2.2 mg/100 kcal to about 22 mg/100 kcal. In other embodiments, N-octanoyl-D-threo-sphingosine may be present in an amount from about 4.4 mg/100 kcal to about 16.3 mg/100 kcal. In another embodiment N-octanoyl-D-threo-sphingosine may be present in an amount from about 7.4 mg/100 kcal to about 14.8 mg/100 kcal. In still other embodiments, N-octanoyl-D-threo-sphingosine may be present in an amount from about 9.6 mg/100 kcal to about 13.3 mg/100 kcal.

In some embodiments the nutritional composition may optionally include choline. If included, choline may be present in an amount from about 4.9 mg/100 kcal to about 43 mg/100 kcal.

Resveratrol may be included in the nutritional composition, in some embodiments in an amount from about 5 mg/100 kcal to about 120 mg/100 kcal. In other embodiments, resveratrol may be present from about 9 mg/100 kcal to about 60 mg/100 kcal.

Resveratrol sources for the present disclosure include, but are not limited to, plant derived extracts, including but not limited to apple extract and grape seed extract. Additionally, non-limiting examples of plants rich in resveratrol suitable for use in the nutritional composition of the present disclosure include: berries (acai, grape, bilberry, blueberry, lingonberry, black currant, chokeberry, blackberry, raspberry, cherry, red currant, cranberry, crowberry, cloudberry, whortleberry, rowanberry), purple corn, purple potato, purple carrot, red sweet potato, red cabbage, eggplant. The resveratrol could be part of a complex mixture obtained by separation technology known in the art aimed at enrichment of the resveratrol and the derivatives or precursors of resveratrol in such mixtures.

Uridine may be present in the nutritional composition in some embodiments, in an amount from about 0.15 mg/100 kcal to about 37 mg/100 kcal. In other embodiments, uridine is present in an amount from about 0.7 mg/100 kcal to about 11.1 mg/100 kcal. In another embodiment, uridine is present in the nutritional composition from about 2.9 mg/100 kcal to about 17.7 mg/100 kcal. In yet other embodiments, uridine is present in an amount from about 14.7 mg/100 kcal to about 22.2 mg/100 kcal. In still yet other embodiments, uridine is present in an amount from about 25.9 mg/100 kcal to about 37 mg/100 kcal.

In some embodiments the nutritional composition(s) disclosed herein further comprises lutein. The lutein as used herein, unless otherwise specified, refers to one or more of free lutein, lutein esters, lutein salts, or other lutein derivatives of related structures as described or otherwise suggested herein. In some embodiments lutein is present from about 0.343 mg/100 kcal to about 6.0 mg/100 kcal. In still other embodiments, lutein is present from about 1.0 mg/100 kcal to about 4.0 mg/100 kcal.

Lutein sources for the present disclosure include, but are not limited to, plant sources rich in carotenoids including, but not limited to kiwi, grapes, citrus, tomatoes, watermelons, papayas and other red fruits, or dark greens, such as kale, spinach, turnip greens, collard greens, romaine lettuce, broccoli, zucchini, garden peas and brussels sprouts, spinach, and carrots. Further, sources for lutein include other plants and any other resources, fortified or not, from which lutein could be obtained and used in a nutritional composition. The lutein could be part of a complex mixture obtained by separation technology known in the art aimed at enrichment of the lutein and the derivatives or precursors of lutein in such mixtures.

Lutein for use herein includes any natural or synthetic source that is known for or is otherwise an acceptable source for use in oral nutritionals, including infant formulas. Lutein sources can be provided as individual ingredients or in any combination with other materials or sources, including sources such as multivitamin premixes, mixed carotenoid premixes, pure lutein sources, and inherent lutein components in the infant formula. The lutein concentrations and ratios as described herein may be calculated based upon both added and inherent lutein sources. In one embodiment, the nutritional composition is an infant formula which comprises at least about 10%, 25%, more preferable from about 50% to about 95%, by weight of total lutein as inherent lutein. In other embodiments, the nutritional composition is an infant formula which preferably comprises at least about 85% lutein by weight of total lutein as inherent lutein.

In one embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included in the composition, the amount of the probiotic may vary from about $1\times10^4$ to about $1.5\times10^{10}$ cfu of probiotics per 100 kcal, more preferably from about $1\times10^6$ to about $1\times10^9$ cfu of probiotics per 100 kcal. In certain other embodiments the amount of probiotic may vary from about $1\times10^7$ cfu/100 kcal to about $1\times10^8$ cfu/100 kcal.

In some embodiments, the nutritional composition may include a source comprising probiotic cell equivalents. In included in the nutritional composition, the amount of the probiotic cell equivalents may vary from about $1\times10^4$ to about $1.5\times10^{10}$ cell equivalents of probiotic(s) per 100 kcal. In some embodiments the amount of probiotic cell equivalents may be from about $1\times10^6$ to about $1\times10^9$ cell equivalents of probiotic(s) per 100 kcal nutritional composition. In certain other embodiments the amount of probiotic cell equivalents may vary from about $1\times10^7$ to about $1\times10^8$ cell equivalents of probiotic(s) per 100 kcal of nutritional composition.

In some embodiments, the probiotic source incorporated into the nutritional composition may comprise both viable colony-forming units, and non-viable cell-equivalents.

In some embodiments, the nutritional composition includes a culture supernatant from a late-exponential growth phase of a probiotic batch-cultivation process. Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of the probiotic. The term "culture supernatant" as used herein, includes the mixture of components found in the culture medium. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In an embodiment, a culture supernatant is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removing liquid contents from the culture supernatant so as to obtain the composition.

The culture supernatant may comprise secreted materials that are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In some embodiments, the culture supernatant is harvested at a point in time of 75% to 85% of the duration of the exponential phase, and may be harvested at about ⅚ of the time elapsed in the exponential phase.

As noted, the disclosed nutritional composition may comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

In some embodiments, the amount of β-glucan in the nutritional composition is between about 3 mg/100 kcal and about 17 mg/100 kcal. In another embodiment the amount of β-glucan is between about 6 mg/100 kcal and about 17 mg/100 kcal.

The nutritional composition may comprise in some embodiments β-1,3;1,6-glucan. The β-1,3;1,6-glucan can be derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

The nutritional composition of the present disclosure, may comprise lactoferrin. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion (Fe3+) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms.

Lactoferrin for use in the present disclosure may be, for example, isolated from the milk of a non-human animal or produced by a genetically modified organism. The nutritional compositions described herein can, in some embodiments comprise non-human lactoferrin, non-human lactoferrin produced by a genetically modified organism and/or human lactoferrin produced by a genetically modified organism.

Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 65% homology with human lactoferrin and in some embodiments, at least 75% homology. Non-human lactoferrins acceptable for use in the present disclosure include, without limitation, bLF, porcine lactoferrin, equine lactoferrin, buffalo lactoferrin, goat lactoferrin, murine lactoferrin and camel lactoferrin.

bLF suitable for the present disclosure may be produced by any method known in the art. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In certain embodiments, lactoferrin utilized in the present disclosure may be provided by an expanded bed absorption ("EBA") process for isolating proteins from milk sources. EBA, also sometimes called stabilized fluid bed adsorption, is a process for isolating a milk protein, such as lactoferrin, from a milk source comprises establishing an expanded bed adsorption column comprising a particulate matrix, applying a milk source to the matrix, and eluting the lactoferrin from the matrix with an elution buffer comprising about 0.3 to about 2.0 M sodium chloride. Any mammalian milk source may be used in the present processes, although in particular embodiments, the milk source is a bovine milk source. The milk source comprises, in some embodiments, whole milk, reduced fat milk, skim milk, whey, casein, or mixtures thereof.

In particular embodiments, the target protein is lactoferrin, though other milk proteins, such as lactoperoxidases or lactalbumins, also may be isolated. In some embodiments, the process comprises the steps of establishing an expanded bed adsorption column comprising a particulate matrix, applying a milk source to the matrix, and eluting the lactoferrin from the matrix with about 0.3 to about 2.0M sodium chloride. In other embodiments, the lactoferrin is eluted with about 0.5 to about 1.0 M sodium chloride, while in further embodiments, the lactoferrin is eluted with about 0.7 to about 0.9 M sodium chloride.

The expanded bed adsorption column can be any known in the art, such as those described in U.S. Pat. Nos. 7,812,138, 6,620,326, and 6,977,046, the disclosures of which are hereby incorporated by reference herein. In some embodiments, a milk source is applied to the column in an expanded mode, and the elution is performed in either expanded or packed mode. In particular embodiments, the elution is performed in an expanded mode. For example, the expansion ratio in the expanded mode may be about 1 to about 3, or about 1.3 to about 1.7. EBA technology is further described in international published application nos. WO 92/00799, WO 02/18237, WO 97/17132, which are hereby incorporated by reference in their entireties.

The isoelectric point of lactoferrin is approximately 8.9. Prior EBA methods of isolating lactoferrin use 200 mM sodium hydroxide as an elution buffer. Thus, the pH of the system rises to over 12, and the structure and bioactivity of lactoferrin may be comprised, by irreversible structural changes. It has now been discovered that a sodium chloride solution can be used as an elution buffer in the isolation of lactoferrin from the EBA matrix. In certain embodiments, the sodium chloride has a concentration of about 0.3 M to about 2.0 M. In other embodiments, the lactoferrin elution buffer has a sodium chloride concentration of about 0.3 M to about 1.5 M, or about 0.5 m to about 1.0 M.

The lactoferrin that is used in certain embodiments may be any lactoferrin isolated from whole milk and/or having a low somatic cell count, wherein "low somatic cell count" refers to a somatic cell count less than 200,000 cells/mL. By way of example, suitable lactoferrin is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand.

Surprisingly, lactoferrin included herein maintains certain bactericidal activity even if exposed to a low pH (i.e., below about 7, and even as low as about 4.6 or lower) and/or high temperatures (i.e., above about 65° C., and as high as about 120° C.), conditions which would be expected to destroy or severely limit the stability or activity of human lactoferrin. These low pH and/or high temperature conditions can be expected during certain processing regimen for nutritional compositions of the types described herein, such as pasteurization. Therefore, even after processing regimens, lactoferrin has bactericidal activity against undesirable bacterial pathogens found in the human gut.

The nutritional composition may, in some embodiments, comprise lactoferrin in an amount from about 10 mg/100 kcal to about 250 mg/100 kcal. In some embodiments, lactoferrin may be present in an amount of from about 50 mg/100 kcal to about 175 mg/100 kcal. Still in some embodiments, lactoferrin may be present in an amount of from about 100 mg/100 kcal to about 150 mg/100 kcal.

The disclosed nutritional composition described herein, can, in some embodiments also comprise an effective amount of iron. The iron may comprise encapsulated iron forms, such as encapsulated ferrous fumarate or encapsulated ferrous sulfate or less reactive iron forms, such as ferric pyrophosphate or ferric orthophosphate.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 μm to 1500 μm, more preferably in the range of 10 μm to 300 μm.

If the nutritional composition is in the form of a ready-to-use product, the osmolality of the nutritional composition may be between about 100 and about 1100 mOsm/kg water, more typically about 200 to about 700 mOsm/kg water.

In certain embodiments, the nutritional composition is hypoallergenic. In other embodiments, the nutritional composition is kosher and/or halal. In still further embodiments, the nutritional composition contains non-genetically modified ingredients. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In embodiments providing a nutritional composition for a child, the composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

In embodiments providing a children's nutritional product, such as a growing-up milk, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the children's nutritional composition may contain between about 10 and about 50% of the maximum dietary recommendation for any given country, or between about 10 and about 50% of the average dietary recommendation for a group of countries, per serving, of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional composition(s) of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, grape and or grape seed extracts, apple extract, bilberry extract or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy or any other plant and animal sources), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, CITREM, and mixtures thereof.

EXAMPLES hADSCs

The hADSCs used in the following procedures are purchased from commercial resources and grown in the maintenance media consisting of Complete MesenPRO RS medium with supplement and L-glutamine. The subculture of hADSCs is performed when cell culture reaches confluence. To passage hADSCs, the following procedure is used: i) aspirate the Complete MesenPRO RS medium from the cells; ii) rinse the surface area of the cell layer with Dulbecco's phosphate buffered saline (DBPS) buffer by adding the DPBS to the side of the vessel opposite the attached cell layer and rocking the vessel back and forth several times; iii) remove the DPBS by aspiration and discard; iv) detach the cells by adding a sufficient volume of pre-warmed trypsin-EDTA solution without phenol red to cover the cell layer; v) incubate at 37° C. for approximately 7 minutes; vi) observe the cells under a microscope to determine if additional incubation is needed; vii) add 3 mL of the maintenance media to the plate, mix the cell suspension, add the suspension to a 15 mL centrifuge tube and centrifuge at 210 g for 5 minutes; viii) determine the total number of cells and percent viability using a hemacytometer; ix) add Complete MesenPRO RS medium to each vessel so that the final culture volume is 0.2 mL-0.5 mL per cm$^2$; x) seed the cells by adding the appropriate volume of cells to each vessel and incubate at 37° C., 5% $CO_2$ and 90% humidity; and xi) three or four days after seeding, completely remove the medium and replace with an equal volume of Complete MesenPRO RS medium.

Coating

Before seeding the passaged hADSCs on fresh culture plates, the surfaces of the cultureware are washed with sterile DPBS solution three times, followed by multiple rinses with sterile water. The first layer of coating is poly-L-ornithine. The coating is prepared by adding 0.1 mg/mL of poly-L-ornithine and incubating at 37° C. for one hour. The plate is washed three times with DPBS, 15 minutes per wash. The second layer of coating is bovine plasma fibronectin. The fibronectin is diluted in DPBS from stock to 1:1000 and 500 μL is added to each well. The plate is left at room temperature for one hour. One final wash with 500 μL per well of DPBS is performed and the plate is used immediately.

Medium hADSCs can be maintained in an undifferentiated state or guided to differentiate using different culture media. Certain culture media are capable of guiding ADSCs to differentiate into neuronal cells. Exemplary media are set forth in Tables 3, 4 and 5.

TABLE 3

Serum-free RNDP medium

| component | Final concentration |
|---|---|
| neural basal medium | 500 mL |
| EGF | 20 ng/mL |
| b-FGF | 20 ng/mL |
| N2 supplement | 1× |
| L-glutamine | 2 mM |

TABLE 4

Serum-free ENDP priming medium

| component | Final concentration |
|---|---|
| neural basal medium | 500 mL |
| EGF | 20 ng/mL |
| bFGF | 20 ng/mL |
| N2 supplement | 1× |

TABLE 5

ENDP differentiation medium

| component | Final concentration |
|---|---|
| MesenPRO complete | 500 mL |

RNDP Protocol

Two independent screening protocols are described, designated as rapid neuronal differentiation platform (RNDP) and extended neuronal differentiation platform (ENDP). The RNDP protocol provides rapid screening of large numbers of candidate compounds, such as cholesterol and/or oxysterol, in a relatively short period of time. RNDP allows the rapid identification of compounds that either promote or inhibit neurogenesis, or that have no effect on neurogenesis. The RNDP may be followed by an ENDP in order to further investigate and confirm the results.

The subculture media of the hADSCs described above is removed from the culture dish, and the dish is then gently washed with 5-10 mL of sterile DPBS. The DPBS is removed and 1.5 mL of trypsin-EDTA is added to completely cover the cell layer. The dish is placed back in the incubator for seven minutes. The plate is then gently tapped to detach cells completely, 3 mL of the maintenance media is added to the plate, and the cell suspension is mixed and added to 15 mL centrifuge tube. The desired cell density ($1 \times 10^4$ cells/well) is taken to another 15 mL tube and placed to centrifuge at 210 g for 5 minutes. The cell pellet is resuspended in an appropriate volume of pre-warmed serum-free rapid neuronal differentiation medium as set forth in Table 1 and seeded onto each well of tissue culture plate. The cholesterol or oxysterol for each well are added sequentially. The plate is put back into the incubator. The effects of cholesterol or oxysterol are quickly and easily observed using phase contrast microscopy images, which are usually taken once immediately before treatment, three hours post treatment and each day thereafter for three days. With a fast turnover time, the best results typically occur within 36 hours. After images are collected, data analysis and comparison is made to determine the effectiveness of each compound or mixture of compounds in modulating neurogenesis. Neuronal differentiation is determined by observing neuronal morphology. Some changes in the cells include shrinking of the cytoplasm, formation of axons and dendrite-like cytoplasmic projections. These changes begin with the cytoplasm of hADSCs retracting toward the nucleus to form contracted cell bodies with cytoplasmic extensions. Cells eventually develop a morphology that resembles bi-polar, tri-polar, and multi-polar neuronal cells.

ENDP Protocol

The ENDP protocol provides a method for further investigation of the results of the RNDP and also allows additional time for priming the hADSCs for further differentiation into various neuronal cell lineages. While not being bound by any particular theory, the priming drives transdifferentiation of the hADSCs from mesoderm lineages to neural ectoderm.

The hADSCs are seeded on culture plates with coated surfaces and grown in the serum-free ENDP priming medium (see table 2) for at least 72 hours. The priming medium is removed and neuronal differentiation medium added (see Table 3) in the presence or absence of either cholesterol or oxysterol. The cultures are then incubated for an extended period of time for further neuronal development. After three days of incubation, the cells are examined under microscope for morphological changes. The percentage and length of neurites can be measured by using open software of Image J with an appropriate plug-in. The cells can further be studied for various neuronal markers to further confirm neuronal differentiation.

Discovery of Brain Nutrients

The purpose of this investigation is to determine the neurogenesis effect of various nutrients (candidate compounds) using both RNDP and ENDP platforms. The candidate compounds herein, are cholesterol and oxysterol. Each are tested individually and compared to the positive control, docosahexaenoic acid (DHA), and the negative control. Pre-warmed serum-free medium contains Neural Basal medium with L-glutamine, 20 ng/mL of b-FGF, 20 ng/mL of EGF and N2 supplement. The candidate compound is added to individual wells at various concentrations in the serum-free medium. The candidate compounds are selected from the group consisting of cholesterol and/or oxysterol. Compounds are tested in varying concentrations, ranging in the nanomolar to micromolar range. The compounds are tested individually and compared to the positive control, docosahexaenoic acid (DHA), and the negative control. The experiments are repeated in triplicate. The nutrients found to promote neurogenesis or demonstrate use as a medicament are further screened in various combinations. These experiments are also repeated in triplicate.

The effects of cholesterol or oxysterol are easily and quickly observed under phase contrast microscopy for up to one week with images usually taken once immediately before treatment with cholesterol or oxysterol, three hours post treatment, and each day thereafter for three days. With a fast turnover time, the best results typically occur within 36 hours. After images are collected, data analysis and comparison is made to determine the effectiveness of cholesterol or oxysterol in promoting neurogenesis. Neuronal differentiation is determined by neuronal morphology. Some of these changes include shrinkage of the cytoplasm, and formation of axons and dendrite-like cytoplasmic projections (neurites). These changes begin with the cytoplasm of hADSCs retracting towards the nucleus to form contracted cell bodies with cytoplasmic extensions. Cells eventually develop a morphology that resembles bi-polar, tri-polar and multi-polar neuronal cells.

Example 1

This example describes the neurogenesis of hADSCs by cholesterol as compared to DHA and a negative control.

Cholesterol was purchased from Sigma-Aldrich, sold as brand of Synthechol® (Cat. #S5542). EPA was diluted in 100% ethanol to a stocking concentration of 33.06 mM.

hADSCs were purchased from Invitrogen, also known as Life Technologies, of Carlsbad, Calif., U.S.A., and were cultured as near confluent monolayers in 100 mm culture plates within a maintenance media consisting of Complete MesenPro RS medium with growth supplement and L-glutamine obtained from Invitrogen®. The process of culturing, passage, and seeding the hADSCs is described below.

The subculture of hADSCs was performed when cell culture reached confluence. To passage hADSCs, the following procedure is used: i) aspirate the Complete MesenPRO RS medium from the cells; ii) rinse the surface area of the cell layer with Dulbecco's phosphate buffered saline (DBPS) buffer by adding the DPBS to the side of the vessel opposite the attached cell layer and rocking the vessel back and forth several times; iii) remove the DPBS by aspiration and discard; iv) detach the cells by adding a sufficient volume of pre-warmed trypsin-EDTA solution without phenol red to cover the cell layer; v) incubate at 37° C. for approximately 7 minutes; vi) observe the cells under a microscope to determine if additional incubation is needed; vii) add 3 mL of the maintenance media to the plate, mix the cell suspension, add the suspension to a 15 mL centrifuge tube and centrifuge at 210 g for 5 minutes; viii) determine the total number of cells and percent viability using a hemacytometer; ix) add Complete MesenPRO RS medium to each vessel so that the final culture volume is 0.2 mL-0.5 mL per $cm^2$; x) seed the cells by adding the appropriate volume of cells to each vessel and incubate at 37° C., 5% $CO_2$ and 90% humidity; and xi) three or four days after seeding, completely remove the medium and replace with an equal volume of Complete MesenPRO RS medium.

Before seeding the passaged hADSCs on fresh culture plates, the surfaces of the culture ware are washed with sterile DPBS solution three times, followed by multiple rinses with sterile water. The first layer of coating is poly-L-ornithine. The coating is prepared by adding about 15 to about 20 μg/mL of poly-L-ornithine and incubating at 37° C. for one hour. The plate is washed three times with DPBS, 15 minutes per wash. The second layer of coating is bovine plasma fibronectin. The fibronectin is diluted in DPBS from stock to 1:1000 and 500 μL is added to each well. The plate is left at room temperature for one hour. One final wash with 500 μL per well of DPBS is performed and the plate is used immediately.

The cells were then subjected to removal and reseeded at a density of $2 \times 10^4$ cells/ml ($1 \times 10^4$ cells/well) onto 24-well culture plates that contained a poly-L-ornithine and bovine plasma fibronectin coating.

Three days after seeding and priming; the culture medium was changed into neuronal differentiation medium. The culture plates were removed from the incubator and all procedures were conducted in a laminar flow hood. The culture medium was completely removed from each well. The hADSCs were then washed with sterile DPBS solution in an amount of about 1 ml per well, to remove excess culture medium. The DPBS solution was removed and replaced with neuronal differentiation medium. The formulation of the neuronal differentiation medium is such that neurogenesis would be attributed to the nutrient and not to the medium. The neuronal differentiation medium used was Neurobasal™ Medium, available from Invitrogen®, which comprises the following ingredients listed below in Table 1.

TABLE 1

Neurobasal ™ Medium

| Components | Molecular Weight | Concentration (mg/L) | mM |
|---|---|---|---|
| Amino Acids | | | |
| Glycine | 75 | 30 | 0.4 |
| L-Alanine | 89 | 2 | 0.0225 |
| L-Arginine hydrochloride | 211 | 84 | 0.398 |
| L-Asparagine-H$_2$O | 150 | 0.83 | 0.00553 |
| L-Cysteine | 121 | 31.5 | 0.26 |
| L-Histidine hydrochloride-H$_2$O | 210 | 42 | 0.2 |
| L-Isoleucine | 131 | 105 | 0.802 |
| L-Leucine | 131 | 105 | 0.802 |
| L-Lysine hydrochloride | 183 | 146 | 0.798 |
| L-Methionine | 149 | 30 | 0.201 |
| L-Phenylalanine | 165 | 66 | 0.4 |
| L-Proline | 115 | 7.76 | 0.0675 |
| L-Serine | 105 | 42 | 0.4 |
| L-Threonine | 119 | 95 | 0.798 |
| L-Tryptophan | 204 | 16 | 0.0784 |
| L-Tyrosine | 181 | 72 | 0.398 |
| L-Valine | 117 | 94 | 0.803 |
| Vitamins | | | |
| Choline chloride | 140 | 4 | 0.0286 |
| D-Calcium pantothenate | 477 | 4 | 0.00839 |
| Folic Acid | 441 | 4 | 0.00907 |
| Niacinamide | 122 | 4 | 0.0328 |
| Pyridoxine hydrochloride | 204 | 4 | 0.0196 |
| Riboflavin | 376 | 0.4 | 0.00106 |
| Thiamine hydrochloride | 337 | 4 | 0.0119 |
| Vitamin B12 | 1355 | 0.0068 | 0.000005 |
| i-Inositol | 180 | 7.2 | 0.04 |
| Inorganic Salts | | | |
| Calcium Chloride (CaCl$_2$) (anhyd.) | 111 | 200 | 1.8 |
| Ferric Nitrate (Fe(NO$_3$)3"9H$_2$O) | 404 | 0.1 | 0.000248 |
| Magnesium Chloride (anhydrous) | 95 | 77.3 | 0.814 |
| Potassium Chloride (KCl) | 75 | 400 | 5.33 |
| Sodium Bicarbonate (NaHCO$_3$) | 84 | 2200 | 26.19 |
| Sodium Chloride (NaCl) | 58 | 3000 | 51.72 |
| Sodium Phosphate monobasic (NaH$_2$PO4—H$_2$O) | 138 | 125 | 0.906 |
| Zinc sulfate (ZnSO$_4$—7H$_2$O) | 288 | 0.194 | 0.000674 |
| Other Components | | | |
| D-Glucose (Dextrose) | 180 | 4500 | 25 |
| HEPES | 238 | 2600 | 10.92 |
| Sodium Pyruvate | 110 | 25 | 0.227 |

Cholesterol was added to individual wells at various concentrations in the serum-free medium. Pre-warmed serum-free medium contains Neural Basal medium with L-glutamine, 20 ng/mL of bFGF, 20 ng/mL of EGF and N2 supplement. See Table 2 below.

TABLE 2

N2 Supplement.

| Components | Molecular Weight | Concentration (mg/L) | mM |
|---|---|---|---|
| Proteins | | | |
| Human transferrin (Holo) | 10000 | 10000 | 1 |
| Insulin recombinant full chain | 5807.7 | 500 | 0.0861 |
| Other components | | | |
| Progesterone | 314.47 | 0.63 | 0.002 |
| Putrescine | 161 | 1611 | 10.01 |
| selenite | 173 | 0.52 | 0.00301 |

Treatments of cholesterol were tested at concentrations of 5 µM and 200µ. Cholesterol in varying concentrations was tested individually and compared to the positive control, DHA, and the negative control (no treatment) under phase contrast microscopy at 24 hours, 48 hours and 96 hours. The experiments were repeated in triplicate.

Figure 1B:
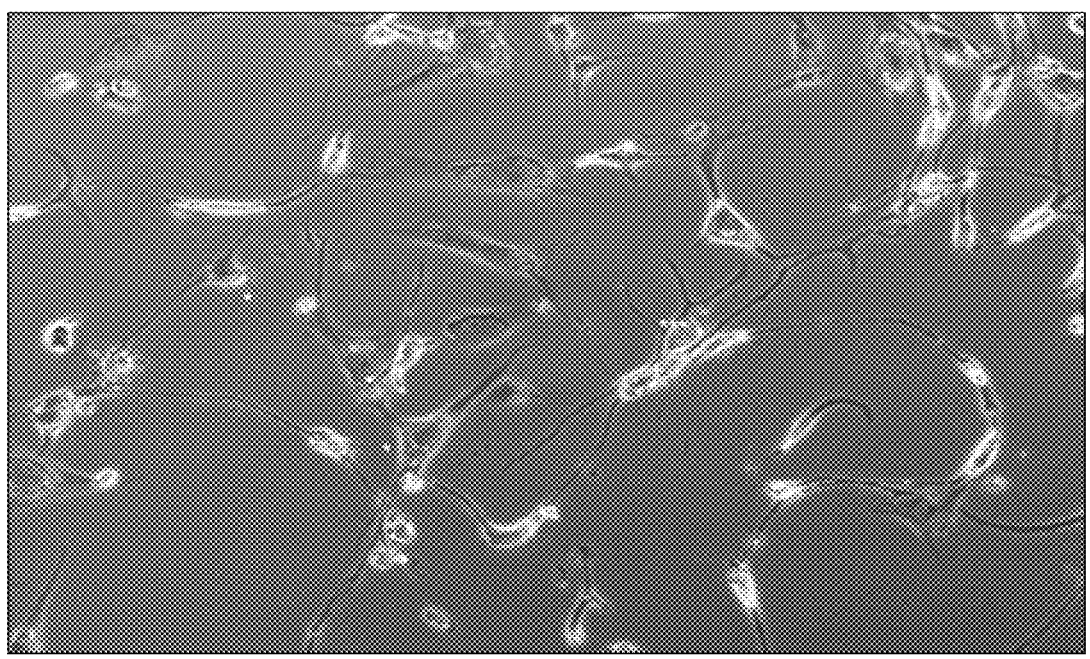
FIG. 1B is a phase contrast microscopy image of hADSCs forming morphology that resembles bi-polar, tri-polar, and multi-polar neural cells.

After images were collected, data analysis and comparison was made to determine the effectiveness of each concentration of cholesterol in promoting neurogenesis. Neuronal differentiation is determined by neuronal morphology. Some of these changes include shrinkage of the cytoplasm, and formation of axons and dendrite-like cytoplasmic projections (neurites). These changes begin with the cytoplasm of hADSCs retracting towards the nucleus to form contracted cell bodies with cytoplasmic extensions. Cells eventually develop a morphology that resembles bi-polar, tri-polar and multi-polar neuronal cells. See FIGS. 1A and 1B.

Figure 2A:
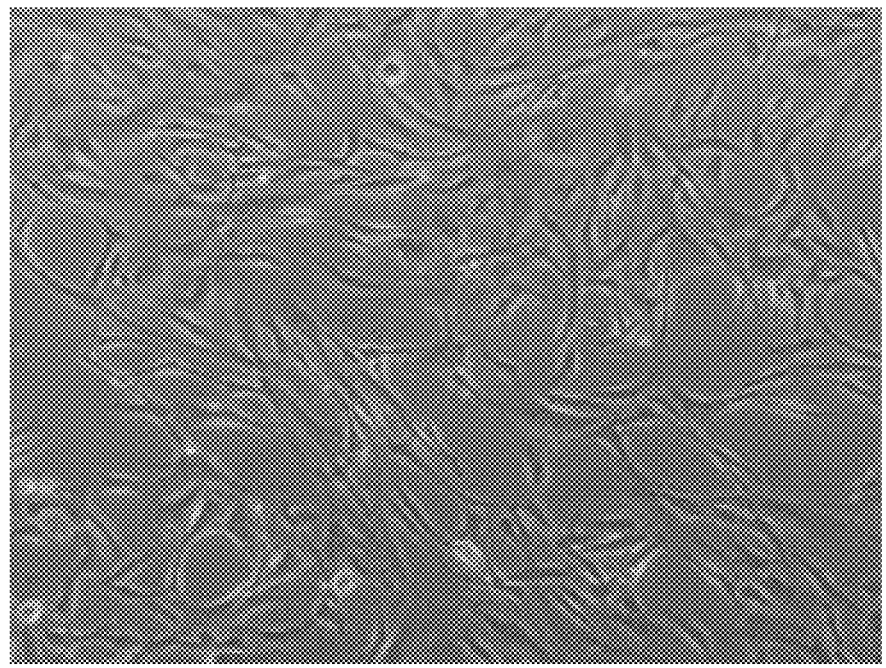
FIG. 2A is a phase contrast microscopy image of a control well containing hADSCs with no treatment of a neurologic component or DHA.

Generally, if the hADSCs display neuronal morphology this result is attributed to the neurogenesis capability of the neurologic component added, in this example cholesterol. For example, the hADSCs in the control wells with no treatment maintained their putative morphology as large, flat and spread cells on the culture surface, suggesting no obvious neurogenesis. See. FIG. 2A.

Figure 2B:
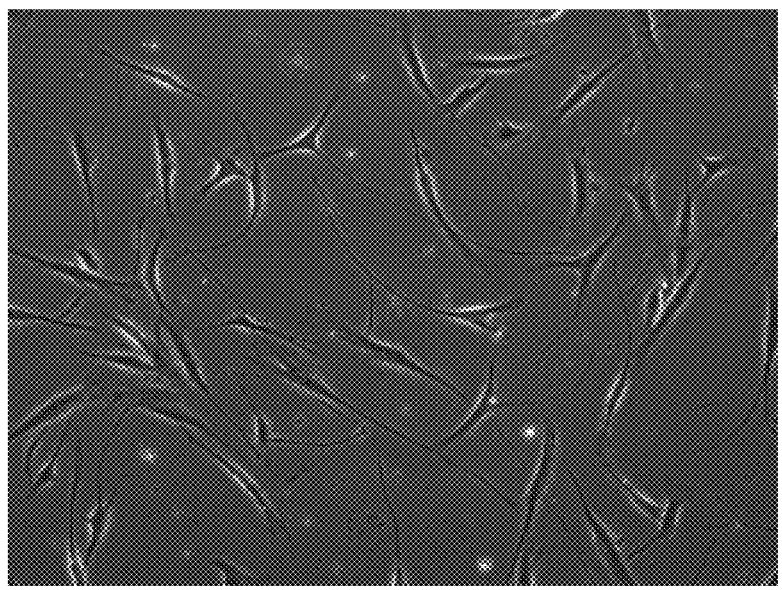
FIG. 2B is a phase contrast microscopy image of a control well containing hADSCs with treatment of cholesterol.

Noticeably, cholesterol at an experimental concentration of 5 µM demonstrated the strongest effect to enhance neurogenesis as shown by the neuronal morphology displayed by the hADSCs in FIG. 2B. The hADSCs treated with cholesterol exhibit long outgrowth with some branching. In light of these results, it was determined that cholesterol can serve as a naturally-occurring nutrient that possesses neurogenesis actions. The addition of cholesterol also promoted neurogenesis when compared to the negative control.

Figure 2C:
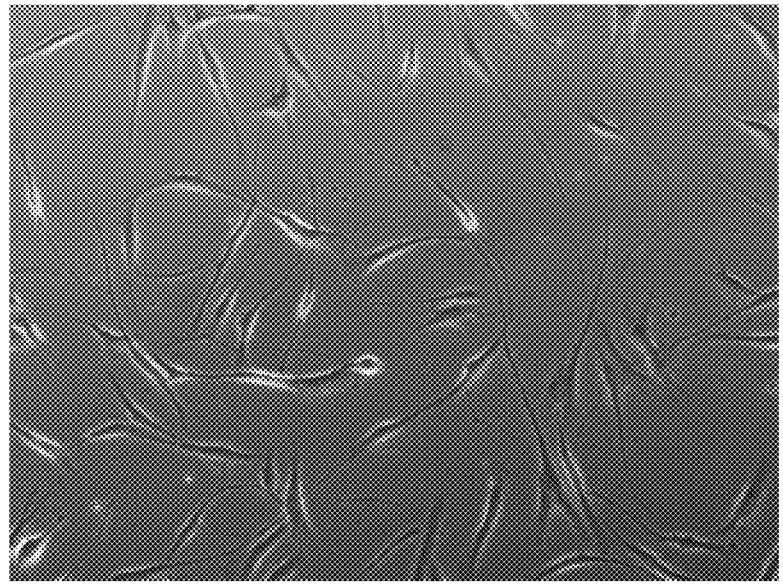
FIG. 2C is a phase contrast microscopy image of a well containing hADSCs with treatment of DHA.

The additions of DHA at 100 µM to hADSCs as a positive control enhanced neuronal morphology of hADSCs when compared to the negative control. See. FIG. 2C. Further, in the presence of DHA at 10 µM, a few of the hADSCs changed dramatically from their putative morphology into neuronal cell morphology as the cytoplasm shrank and neurites began to protrude from the hADSCs.

Example 2

This example describes the neurogenesis of hADSCs by 7β-oxysterol as compared to DHA and a negative control.

Figure 3A:
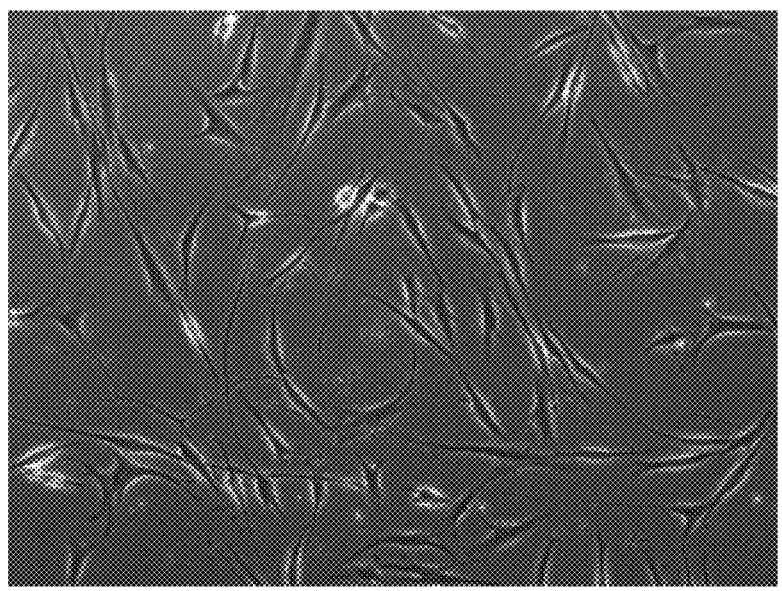
FIG. 3A is a phase contrast microscopy image of a well containing hADSCs with treatment of 7β-oxysterol.

7β-oxysterol was diluted in 100% ethanol. The hADSCs were cultured, passaged, seeded and subjected to sphingomyelin via the same procedure outlined in Example 1.

hADSCs treated with 7β-oxysterol underwent significant neurogenesis displaying neuronal morphological changes, including neurite outgrowth and cytoplasm shrinking. See FIG. 3A.

Example 3

Additionally, cholesterol promotes neurogenesis on human neuronal stem cells ("hNSCs") line. Disclosed herein is the method for testing neurogenesis of cholesterol on hNSCs and the results obtained.

Briefly, hNSCs were purchased from Millipore, Bellerica, Mass., U.S.A., with genetic modification to constitutively express green fluorescent protein ("GFP"). The hNSCs were cultured on laminin coated plates as recommended by the manufacturer. Both laminin and DEME/F12 were obtained from Millipore. Laminin was diluted with DMEM/F12 to 20 µg/mL. 10 ml of diluted laminin solution was added to 10 cm tissue culture dish. Then the culture dish was incubated in a 37° C., 5% CO2 incubator overnight. Just before use, the laminin solution was aspirated and rinsed once with sterile DPBS solution. hNSCs were cultured in the ReNcell NSC maintenance medium (Millipore) supplied with 20 ng/mL bFGF and 20 ng/mL EGF in a 37° C., 5% $CO_2$ incubator. Medium was exchanged with fresh medium containing bFGF and EGF every other day thereafter. The cells reached 80% confluence 2 to 3 days after this step.

After hNSCs reach 80% confluence, hNSCs were ready for the differentiation experiment. Before seeding, a 96-well plate was freshly coated with 20 μg/mL laminin solution followed by a brief DPBS rinse as described above. Culture medium was removed carefully and hNSCs were dissociated within 3 ml Accutase (Millipore) in a 37° C., 5% $CO_2$ incubator for 3 minutes. Then 5 ml of ReNcell NSC maintenance medium (Millipore) supplied with 20 ng/mL bFGF and 20 ng/mL EGF were added. The cell suspension was then transferred a sterile 15 ml conical tube and the cells were pelleted by the centrifugation at 300×g for 5 minutes. Supernatant was removed. 2 ml medium was then applied to the tube and hNSCs was resuspended thoroughly. The hNSCs were seeded on a 96-well plate at a density of $1 \times 10^4$ cell/ml (1000 cells/well, 100 μl/well).

After attaching to the culture surface, the culture medium was switched to serum-free differentiation medium in the presence of cholesterol, or DHA, or no treatment. The serum-free differentiation medium was prepared freshly before the switching including 40 ml DMEM/F12 (Millipore), 400 μl L-Glutamine at a concentration of 200 mM (Life Technologies, Carlsbad, Calif.), 400 μl B27 solution (Life Technologies, Carlsbad, Calif.), and 40 μl Heperin (Sigma-Aldrich, St. Louis, Mich.) solution at a concentration of 10 mg/mL.

The cells were observed for morphological changes after 72 hours under inverted fluorescent microscopy. The entire 96-well plate was placed under the Leica DMI4000B fluorescent microscopy, and images were taken with GFP filter under a microscope with UV light source.

Figure 4A:
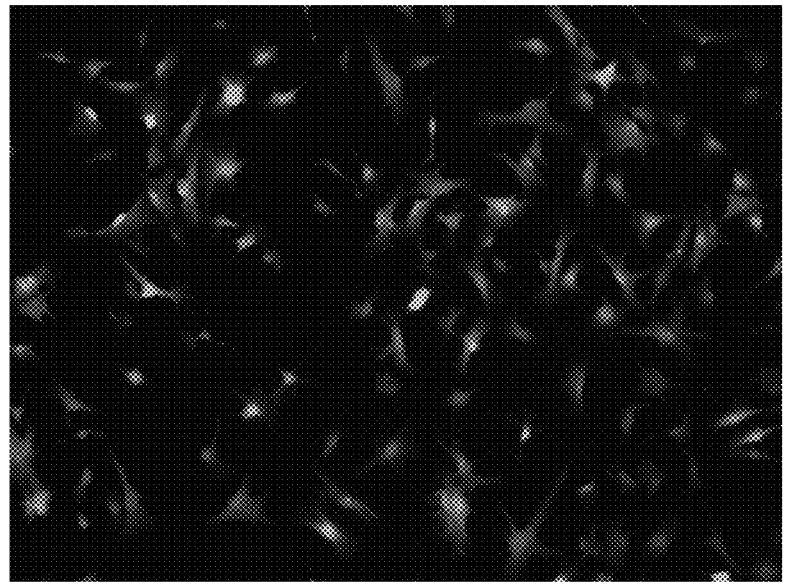
FIG. 4A is an inverted fluorescent phase microscopy image of hNSCs treated with no treatment of DHA or a neurologic component.
Figure 4B:
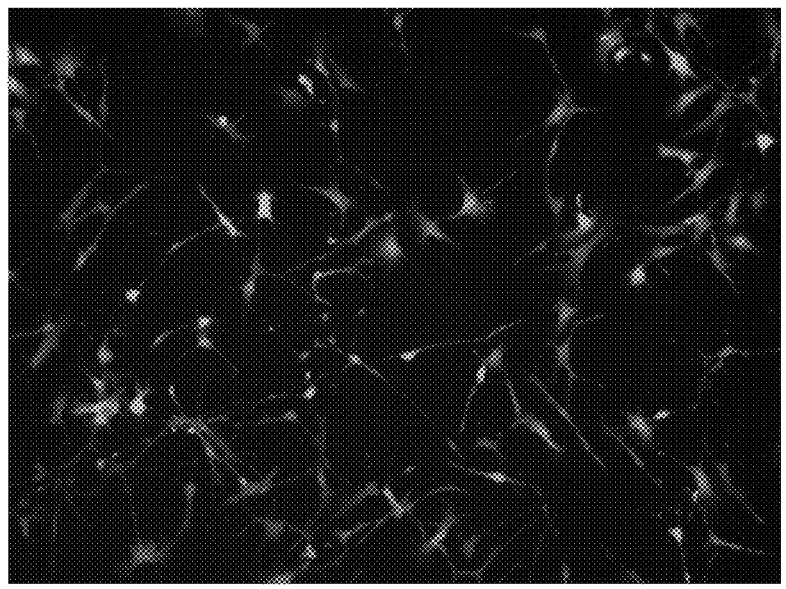
FIG. 4B is an inverted fluorescent phase microscopy image of hNSCs treated with cholesterol.

Cholesterol at 25 μM dramatically promoted neurogenesis when compared to no treatment. See FIG. 4A as compared FIG. 4A. The hNSCs observed had shrinking cellular bodies, projecting neurities and were developing dendrites. See FIG. 4A. The length of neurite outgrowth in the presence of cholesterol is comparable to DHA at 20 μM which demonstrates good effects on neurogenesis. See FIG. 4A and FIG. 4B.

Figure 4C:
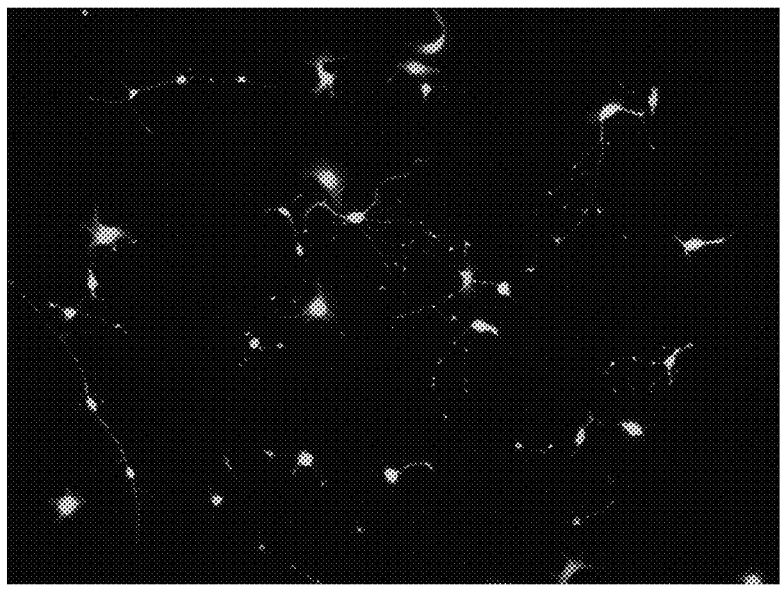
FIG. 4C is an inverted fluorescent phase microscopy image of hNSCs treated with cholesterol and other brain nutrients.

The morphological changes shown in FIG. 4C, illustrates the neuronal morphological changes of hNSCs after treatment with cholesterol and other brain nutrients. These morphological changes include the appearance of more oligodendrocyte differentiation, which suggest myelination function.

Formulation Examples

Table 6 provides an example embodiment of a nutritional composition according to the present disclosure and describes the amount of each ingredient to be included per 100 kcal serving.

TABLE 6

Nutrition profile of an example nutritional composition

| | per 100 kcal | |
| --- | --- | --- |
| Nutrient | Minimum | Maximum |
| Protein (g) | 1.8 | 6.8 |
| Fat (g) | 1.3 | 7.2 |
| Carbohydrates (g) | 6 | 22 |

TABLE 6-continued

Nutrition profile of an example nutritional composition

| | per 100 kcal | |
| --- | --- | --- |
| Nutrient | Minimum | Maximum |
| Prebiotic (g) | 0.3 | 1.2 |
| DHA (g) | 4 | 22 |
| Beta glucan (mg) | 2.9 | 17 |
| cholesterol (mg) | 1 | 100 |
| oxysterol (mg) | 1 | 100 |
| Probiotics (cfu) | $9.60 \times 10^5$ | $3.80 \times 10^8$ |
| Vitamin A (IU) | 134 | 921 |
| Vitamin D (IU) | 22 | 126 |
| Vitamin E (IU) | 0.8 | 5.4 |
| Vitamin K (mcg) | 2.9 | 18 |
| Thiamin (mcg) | 63 | 328 |
| Riboflavin (mcg) | 68 | 420 |
| Vitamin B6 (mcg) | 52 | 397 |
| Vitamin B12 (mcg) | 0.2 | 0.9 |
| Niacin (mcg) | 690 | 5881 |
| Folic acid (mcg) | 8 | 66 |
| Panthothenic acid (mcg) | 232 | 1211 |
| Biotin (mcg) | 1.4 | 5.5 |
| Vitamin C (mg) | 4.9 | 24 |
| Choline (mg) | 4.9 | 43 |
| Calcium (mg) | 68 | 297 |
| Phosphorus (mg) | 54 | 210 |
| Magnesium (mg) | 4.9 | 34 |
| Sodium (mg) | 24 | 88 |
| Potassium (mg) | 82 | 346 |
| Chloride (mg) | 53 | 237 |
| Iodine (mcg) | 8.9 | 79 |
| Iron (mg) | 0.7 | 2.8 |
| Zinc (mg) | 0.7 | 2.4 |
| Manganese (mcg) | 7.2 | 41 |
| Copper (mcg) | 16 | 331 |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

We claim:

1. A method for the promoting neurogenesis in an infant, wherein neurogenesis is promoted in the infant administered the nutritional composition by a change in cell morphology selected from the group consisting of shrinkage of cytoplasm, formation of a neurite, formation of dendrite-like projection, and formation of an axon, as compared to an infant not administered the nutritional composition, wherein the method comprises the step of:

administering to the infant a nutritional composition comprising per 100 kcal:
   from about 6 g to about 22 g carbohydrate source;
   from about 1.3 g to about 7.2 g fat source;
   from about 1.8 g to about 6.8 g a protein source; and
   from about 5 mg about 100 mg of a neurologic component, wherein the neurologic component comprises at least 5 mg cholesterol and at least 5 mg of at least one oxysterol.

2. The method of claim 1, wherein the nutritional composition comprises per 100 kcal from about 10 mg to 250 mg lactoferrin.

3. The method of claim 1, wherein the nutritional composition comprises per 100 kcal from about 2.9 mg to about 17 mg β-glucan.

4. The method of claim 1, wherein the nutritional composition comprises per 100 kcal from about 0.2 g to about 0.6 g polydextrose.

5. The method of claim 1, wherein the nutritional composition comprises per 100 kcal 0.1 g to 1 g galacto-oligosaccharide.

6. The method of claim 1, wherein the nutritional composition is an infant formula.

7. The method of claim 1, wherein the nutritional composition comprises per 100 kcal from about 0.5 mg to about 45 mg sialic acid.

8. The method of claim 1, wherein the protein source comprises hydrolyzed proteins having a degree of hydrolysis of between about 4% and 10%.

9. The method of claim 1, wherein the protein source comprise from about 40% to about 85% whey protein and from about 15% to about 60% casein.

10. The method of claim 1, wherein the protein source comprise extensively hydrolyzed protein.

11. The method of claim 1, wherein the nutritional composition further comprises per 100 kcal from about 5 mg to about 100 mg arachidonic acid.

12. The method of claim 11, wherein the nutritional composition comprises a weight ratio of arachidonic acid to docosahexaenoic acid of between about 1:2 to about 9:1.

13. The method of claim 1, wherein the nutritional composition comprise per 100 kcal from about $9.60 \times 10^5$ to about $3.80 \times 10^8$ CFU of probiotics.

* * * * *